(12) United States Patent
Prado et al.

(10) Patent No.: US 10,238,502 B2
(45) Date of Patent: Mar. 26, 2019

(54) DEVICES, METHODS, SYSTEMS, AND KITS FOR THE SURGICAL TREATMENT OF CERVICAL DISC DISEASE

(71) Applicant: Xenco Medical LLC, San Diego, CA (US)

(72) Inventors: Gustavo R. Prado, San Diego, CA (US); Jason Haider, San Diego, CA (US)

(73) Assignee: Xenco Medical LLC, San Diego, CA (US)

( * ) Notice: Subject to any disclaimer, the term of this patent is extended or adjusted under 35 U.S.C. 154(b) by 172 days.

(21) Appl. No.: 14/928,736

(22) Filed: Oct. 30, 2015

(65) Prior Publication Data

US 2016/0262905 A1    Sep. 15, 2016

Related U.S. Application Data

(60) Provisional application No. 62/133,134, filed on Mar. 13, 2015.

(51) Int. Cl.
*A61F 2/44*    (2006.01)
*A61B 17/70*   (2006.01)
(Continued)

(52) U.S. Cl.
CPC .......... *A61F 2/447* (2013.01); *A61B 17/7059* (2013.01); *A61B 17/8042* (2013.01);
(Continued)

(58) Field of Classification Search
CPC .......... A61F 2/44; A61F 2/4455; A61F 2/446; A61F 2/4465; A61F 2/447; A61F 2/46; A61F 2/4603; A61F 2/4611; A61F 2/4637; A61B 17/7059; A61B 17/8033; A61B 17/8042
(Continued)

(56) References Cited

U.S. PATENT DOCUMENTS 6,837,905 B1    1/2005  Lieberman
8,690,928 B1    4/2014  Walkenhorst et al.
(Continued)

FOREIGN PATENT DOCUMENTS

WO    WO-2016149141 A1    9/2016

OTHER PUBLICATIONS

PCT/US2016/022193 International Search Report and Written Opinion dated Jun. 10, 2016.

*Primary Examiner* — Si Ming Ku
(74) *Attorney, Agent, or Firm* — Wilson Sonsini Goodrich & Rosati

(57) ABSTRACT

Described herein are devices, methods, systems, and kits configured for use in the surgical treatment of cervical disc disease. Surgery for cervical disc disease may comprise vertebral fixation with screws and plates as well as insertion of one or more intervertebral implants. In some embodiments, a cervical implant may be connected as one single unit with a cervical plate. In some embodiments, a cervical implant and a cervical plate may be separate elements that are configured to be inserted independently into a subject during cervical spinal surgery. In some embodiments, a cervical implant and a cervical plate are designed to be coupled together.

6 Claims, 34 Drawing Sheets

(51) Int. Cl.
*A61F 2/46* (2006.01)
*A61B 17/80* (2006.01)
*A61F 2/30* (2006.01)

(52) U.S. Cl.
CPC .......... *A61F 2/4611* (2013.01); *A61F 2/4637* (2013.01); *A61F 2002/30904* (2013.01); *A61F 2002/448* (2013.01); *A61F 2002/4475* (2013.01); *A61F 2002/4642* (2013.01)

(58) Field of Classification Search
USPC ..................................................... 623/17.16
See application file for complete search history.

(56) References Cited

U.S. PATENT DOCUMENTS

| | | |
|---|---|---|
| 8,940,030 B1 | 1/2015 | Stein et al. |
| 2002/0147450 A1* | 10/2002 | LeHuec ............. A61B 17/1671 606/86 B |
| 2005/0085913 A1* | 4/2005 | Fraser ................ A61B 17/7059 623/17.11 |
| 2009/0182430 A1* | 7/2009 | Tyber ................... A61F 2/4465 623/17.16 |
| 2010/0145460 A1 | 6/2010 | McDonough et al. |
| 2014/0058446 A1 | 2/2014 | Bernstein |
| 2015/0025635 A1* | 1/2015 | Laubert .................. A61F 2/447 623/17.16 |

\* cited by examiner

DEVICES, METHODS, SYSTEMS, AND KITS FOR THE SURGICAL TREATMENT OF CERVICAL DISC DISEASE

This application claims the benefit of U.S. Provisional Patent Application No. 62/133,134, filed, Mar. 13, 2015, which is hereby explicitly incorporated herein by reference in its entirety.

BACKGROUND

Cervical disc disease is a prevalent disease that may be caused by, for example, degeneration of the intervertebral discs in the cervical spine or by traumatic injury and accompanying disc rupture or damage. Cervical discs function to, for example, provide cushioning to the cervical vertebrae, absorb compressive force on the neck and spine, and provide proper spacing between the cervical vertebrae. Degeneration, rupture, or other damage to the intervertebral discs may cause anatomical changes to the spine which may cause severe radiculopathy when, for example, a cervical spinal nerve is compressed due to the change in normal anatomy caused by one or more degenerated, ruptured, or otherwise damaged intervertebral disc. Radiculopathy caused by spinal nerve compression may be severe and debilitating.

Surgical treatment for cervical disc disease may include insertion of a cervical implant in the disc space where, for example, a degenerated, ruptured, or damaged intervertebral disc is located. Placement of an implant may be combined with fixation of two or more vertebrae. Vertebral fixation alone may be performed as well.

SUMMARY

Described herein are devices, methods, systems, and kits configured for use in the surgical treatment of cervical disc disease. Surgery for cervical disc disease may comprise vertebral fixation with screws and plates as well as insertion of one or more intervertebral implants. In some embodiments, a cervical implant may be connected as one single unit with a cervical plate. In some embodiments, a cervical implant and a cervical plate may be separate elements that are configured to be inserted independently into a subject during cervical spinal surgery. In some embodiments, a cervical implant and a cervical plate are designed to be coupled together.

Described herein are devices, methods, systems, and kits that are configured to provide the ability to effectively and more easily perform a surgical treatment for cervical disc disease.

Described herein is a system for use in surgical treatment of cervical disc disease comprising a cervical implant comprising a cervical implant coupler, wherein said cervical implant is configured to be positioned between a first and a second cervical vertebra; and a cervical plate comprising one or more surgical screw holes, wherein the one or more surgical screw holes are configured to receive a screw; a first cervical plate coupler configured to couple the cervical plate to the cervical implant; wherein the cervical implant coupler and the first cervical plate coupler are configured to couple together in a snap-fit fashion. In some embodiments, the cervical implant coupler comprises an opening, wherein at least one distance measured across said opening is narrower than a widest width of said cervical plate coupler. In some embodiments, the one or more screw holes comprise one or more angled interior edges that are configured to seat a received screw at an angle that is not perpendicular to the cervical plate when the cervical plate is coupled with the cervical implant. In some embodiments, the cervical plate coupler comprises one or more prongs. In some embodiments, the cervical plate coupler comprises two prongs, wherein the widest distance between the two prongs comprises a first width when the prongs are not compressed, and wherein the widest distance between the two prongs comprises a second width when the two prongs are compressed, wherein the second width is smaller than the first width, and wherein the second width is smaller than at least one width of an opening in a cervical implant coupler. In some embodiments, the system further comprises a blocking cap comprising a blocking cap coupler, and wherein the blocking cap is configured to prevent the backing out of one or more screws when coupled with a cervical plate. In some embodiments, the cervical plate further comprises a second cervical plate coupler configured to couple with a blocking cap coupler, and wherein the cervical plate further comprises a recessed surface configured to receive the blocking cap and seat the blocking cap at least partially directly over the one or more screws seated within the one or more holes in the cervical plate. In some embodiments, the cervical plate and the blocking cap are configured to couple in a snap-fit fashion. In some embodiments, the cervical plate comprises one or more materials selected from the group consisting of polyether ether ketone (PEEK), carbon fiber-reinforced polymer, carbon fiber-reinforced plastic, carbon fiber-reinforced thermoplastic, glass fiber-reinforced polymer, glass fiber-reinforced plastic and polyaryletherketone.

Described herein is a system for use in surgical treatment of cervical disc disease comprising a cervical plate comprising one or more surgical screw holes, wherein the one or more surgical screw holes are configured to receive a screw; a cervical plate coupler; and a blocking cap comprising a blocking cap coupler configured to couple with the cervical plate coupler, wherein the blocking cap is configured to prevent backing out of one or more screws received by the one or more surgical screw holes of the cervical plate; and wherein the cervical plate and the blocking cap are configured to couple together in a snap-fit fashion. In some embodiments, the cervical plate coupler comprises an opening, wherein at least one distance measured across said opening is narrower than a widest width of the cervical plate coupler. In some embodiments, the one or more screw holes comprise one or more angled interior edges that are configured to seat a received screw at an angle that is not perpendicular to the cervical plate when the cervical plate is coupled with the cervical implant. In some embodiments, the blocking cap coupler comprises one or more prongs. In some embodiments, the blocking cap coupler comprises two prongs, wherein the widest distance between the two prongs comprises a first width when the prongs are not compressed, and wherein the widest distance between the two prongs comprises a second width when the two prongs are compressed, and wherein the second width is smaller than the first width. In some embodiments, the second width is smaller than at least one width of an opening in a cervical plate coupler. In some embodiments, the cervical plate further comprises a recessed surface configured to receive the blocking cap and seat the blocking cap at least partially directly over the one or more screws received within the one or more holes in the cervical plate.

Described herein is a cervical plate for use in surgical treatment of cervical disc disease comprising one or more surgical screw holes, wherein the one or more surgical screw holes are configured to receive a screw; a cervical plate coupler configured to snap-fit with a different coupler; and a recessed surface extending at least partially over the one or more surgical screw holes. In some embodiments, the one or more screw holes comprise one or more angled interior edges that are configured to seat a received screw at an angle that is not perpendicular to the cervical plate when the cervical plate is coupled with the cervical implant. In some embodiments, the coupler comprises two prongs, wherein the widest distance between the two prongs comprises a first width when the prongs are not compressed, and wherein the widest distance between the two prongs comprises a second width when the two prongs are compressed, and wherein the second width is smaller than the first width. In some embodiments, the coupler comprises an opening, wherein at least one width across said opening is narrower than a width of the different coupler.

Described herein is a kit for use in surgical treatment of disc disease comprising a cervical implant comprising a cervical implant coupler, wherein said cervical implant is configured to be positioned between a first and a second cervical vertebra; a cervical plate comprising one or more surgical screw holes, wherein the one or more surgical screw holes are configured to receive a screw; a cervical plate coupler configured to couple the cervical plate to the cervical implant; a blocking cap comprising a blocking cap coupler configured to couple with a cervical plate coupler; a delivery device for delivering the cervical implant to the intervertebral space wherein the cervical implant and the cervical plate are configured to couple together in a snap-fit fashion. In some embodiments, the one or more screw holes comprise one or more angled interior edges that are configured to seat a received screw at an angle that is not perpendicular to the cervical plate when the cervical plate is coupled with the cervical implant. In some embodiments, the cervical plate coupler comprises two prongs, wherein the widest distance between the two prongs comprises a first width when the prongs are not compressed, and wherein the widest distance between the two prongs comprises a second width when the two prongs are compressed, and wherein the second width is smaller than the first width. In some embodiments, the coupler comprises an opening, wherein at least one width across said opening is narrower than a width of the different coupler.

Described herein is a method for use in surgical treatment of disc disease inserting a cervical implant comprising a cervical implant coupler in the intervertebral space between a first and a second vertebra; coupling a cervical plate comprising one or more screw holes and a cervical plate coupler to the cervical implant by snap-fitting the cervical plate coupler with the cervical implant coupler; securing the cervical plate to the first and second vertebra via one or more screws respectively passed through the one or more screw holes and into either the first or the second vertebra; and coupling a blocking cap comprising a blocking cap coupler with the cervical plate by snap-fitting the blocking cap coupler with the cervical plate coupler.

BRIEF DESCRIPTION OF THE DRAWINGS

The novel features of the subject matter described herein are set forth with particularity in the appended claims. A better understanding of the features and advantages of the present subject matter will be obtained by reference to the following detailed description that sets forth illustrative embodiments, in which the principles of the subject matter described herein are utilized, and the accompanying drawings of which:

DETAILED DESCRIPTION

Figure 1:
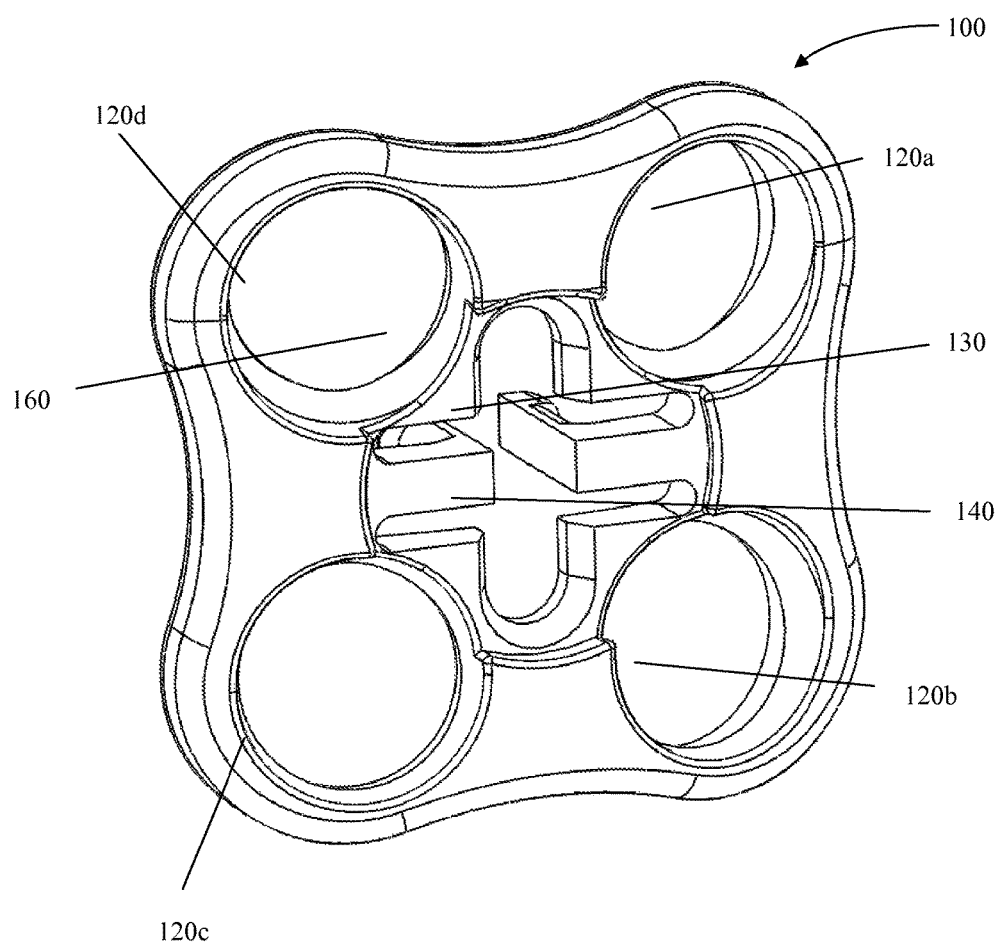
FIG. 1 shows an anterior view of an embodiment of a cervical plate.

Provided herein are devices, methods, systems, and kits configured for use in surgical cervical disc repair. Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The term "subject" as used herein may refer to a human subject or any animal subject.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Provided herein are embodiments related to cervical plates and related medical devices for the securing of a cervical implant into an individual undergoing or having undergone spine surgery such as spine surgery related to the insertion of an intervertebral cervical implant.

In some embodiments, a cervical plate, such as a cervical plate having a plurality of screw holes and a snap-fit coupler, such as a two-pronged snap-fit interface that fixes the cervical plate in place upon insertion into a cavity of a cervical implant. In some embodiments the cervical plate comprises four screw holes, while in alternate embodiments the plate comprises 2, 3, 5, 6, or more than 6 screw holes.

In some embodiments, a snap-fit coupler may comprise two prongs. In some embodiments, the snap-fit coupler comprises 3, 4, 5, 6, 7, 8, or more than 8 prongs. In some embodiments, the prongs are located near the center of the cervical plate. In some embodiments, the prongs are located 1 to 10 mm from the center of the cervical plate, for example 1 mm, 2 mm, 3 mm, 4 mm, 5 mm, 6 mm, 7 mm, 8 mm, 9 mm or 10 mm or any non-integer value within said range of 1 to 10 mm.

In some embodiments, the prongs comprise one or more prong heads, such that insertion of the prongs into a cavity such as a cervical implant cavity is secured through the one or more prong heads 'snapping' into place in an interior space within the cavity having a width greater than the width of the opening of the cavity. In some embodiments, the prong heads are made of the same material as the rest of the cervical plate. In some embodiments, the prong heads are made of a deformable material that is softer than the rest of the cervical plate. In some embodiments, the prong heads are 0.1 to 1 mm larger than the prongs for example 0.1 mm, 0.2 mm, 0.3 mm, 0.4 mm, 0.5 mm, 0.6 mm, 0.7 mm, 0.8 mm, 0.9 mm or 1 mm or any non-integer value within said ranch of 0.1 to 1 mm.

In some embodiments, the prongs extend at right angles from the surface of the cervical plate. In some embodiments the prongs extend away from or towards each other at an angle greater than 90 degrees from the surface of the cervical plate. In some embodiments, the prongs extend at 90-95 degrees, 95-100 degrees, 100-105 degrees, 105-110 degrees, 110-120 degrees, 120-130 degrees or 130-135 degrees from the surface of the cervical plate or any non-integer value within said range of 90 to 135 degrees.

In some embodiments, the prongs are attached to the plate through attachment arms parallel to the plate surface and perpendicular to the prong arms, and extending into an interior opening in the cervical plate, such that In some embodiments the prongs are provided with a degree of flexibility greater than expected in light of their length. In some embodiments the prongs possess an elastic flexibility such that they can be forced through a cavity having an opening smaller than the distance from one prong head edge to the opposite prong head edge, and return to their original positions so as to snap back into position in an internal chamber of the cavity so that the cervical plate is not easily removed once the prongs have snapped into place. In some embodiments, the prongs can flex 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees or more from their original position or any non-integer value within said range of 1 to 15 degrees. In some embodiments, the prongs are made from the same material as the rest of the cervical plate. In other embodiments, the prongs are made of a material more flexible than the rest of the cervical plate.

In some embodiments, the cervical plate is secured such that it cannot move along any axis. In alternate embodiments the cervical plate cannot be easily translated upon an axis perpendicular to the plate face, but the plate face toggles with a modest degree of freedom about an insertion point. In some embodiments, the cervical plate can toggle 0.1 mm, 0.2 mm, 0.3 mm, 0.4 mm, 0.5 mm, 0.6 mm, 0.7 mm, 0.8 mm, 0.9 mm or 1 mm about an insertion point or any non-integer value within said range of 0.1 to 1 mm. In some embodiments the cervical plate 'wobbles' upon insertion of the prongs, but cannot be easily removed from the cervical implant.

In some embodiments, a cervical plate comprises one or more holes, such as screw holes through which one or more securing screws are threaded. In some embodiments, the securing screws are bone screws. In some embodiments, the screw holes measure 1 mm, 2 mm, 3 mm, 4 mm, 5 mm, 6 mm, 7 mm, 8 mm, 9 mm, 10 mm, 12 mm or 15 mm in diameter or any integer or non-integer value within said range of 1 to 15 mm. In some embodiments, the screw holes are threaded. In some embodiments one or more securing screws pass through the cervical plate's one or more screw holes and penetrate vertebral bone, such as vertebral bone above and below a space into which a cervical implant is inserted. In some embodiments, the securing screws are 5 mm, 6 mm, 7 mm, 8 mm, 9 mm, 10 mm, 11 mm, 12 mm, 13 mm, 14 mm or 15 mm in length or any non-integer value within said range of 5 to 15 mm.

In some embodiments, the cervical plate is adjustable such that it can toggle to accommodate a configuration that reflects a tight fit of the one or more screws into the vertebral bone above and below vertebral bone, such as vertebral bone above and below a cervical implant. In some embodiments the screw holes are positioned so as to direct the screws into divergent positions relative to one another, such that the screw tips on opposite sides of a cervical implant are farther from one another than the screw heads are from one another when the screws are threaded through the screw holes at an angle greater than 90 degrees from the surface of the cervical plate. In some embodiments, the screws extend at 90-95 degrees, 95-100 degrees, 100-105 degrees, 105-110 degrees, 110-120 degrees, 120-130 degrees or 130-145 degrees from the surface of the cervical plate or any integer or non-integer value within said range of 90 to 145 degrees. In other embodiments, the screw holes are positioned so as to direct the screws into convergent positions relative to one another, such that the screw tips on opposite sides of a cervical implant are closer to one another than the screw heads are from one another when the screws are threaded through the screw holes at an angle less than 90 degrees from the surface of the cervical plate. In some embodiments, the screw heads extend at 85-90 degrees, 80-85 degrees, 75-80 degrees, 70-75 degrees, 65-70 degrees, 60-65 degrees, 55-60 degrees, 50-55 degrees, 45-50 degrees from the surface of the cervical plate or any integer or non-integer value within said range of 45 to 90 degrees.

In some embodiments, the cervical plate has a size and shape to allow it to be secured to at least two cervical vertebrae. In some embodiments, the cervical plate is rectangular, square or trapezoidal in shape. In some embodiments, the cervical plate has curved corners. In some embodiments, the cervical plate has concave sides. In some embodiments, the cervical plate has four sides of equal length. In some embodiments, the cervical plate has two sides of first length and two sides of a second length, which is greater or smaller than the first length. In some embodiments, the first length is 1 cm, 2 cm, 3 cm, 4 cm, 5 cm, 6 cm, 7 cm in length or any non-integer value within said range of 1 to 7 cm. In additional aspects, the second length is 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22, mm, 23 mm, 24 mm, 25 mm in length or any non-integer value within said range of 5 to 25 mm.

In some embodiments screws are securely inserted into vertebral bone. However, not uncommonly, one or more screws loosen or become disengaged from vertebral bone. If a crew becomes disengaged, surgical intervention is sometimes necessary to secure the cervical plate and screw.

In some embodiments, a cervical plate comprises an interior opening. In some embodiments, the interior opening is round. In additional aspects, the opening is rectangular, square or trapezoidal in shape. In some embodiments, the interior opening is 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm in diameter or any non-integer value within said ranch of 1 to 20 mm. In some embodiments, the interior opening is smaller than a blocking cap. In some aspects the interior opening serves as an interface for a blocking cap, such as a blocking cap comprising one, two, three, four, five, six, seven, eight or more than eight blocking cap prongs.

In some embodiments, a blocking cap comprises one or prongs which may further comprise one or more prong heads, such that insertion of the blocking cap prong or prongs into an interior opening or cavity of a cervical plate that has an interior opening width that matches the distance from the edges of the prongs results in securing the blocking cap when the prong heads pass through the interior opening such that the prong heads are positioned into a locally wider location. In some embodiments, the prong heads are made of the same material as the rest of the blocking cap. In some embodiments, the prong heads are made of a material softer or more deformable than the rest of the blocking cap. In some embodiments, the prong heads are 0.1 to 1 mm larger than the prongs for example 0.1 mm, 0.2 mm, 0.3 mm, 0.4 mm, 0.5 mm, 0.6 mm, 0.7 mm, 0.8 mm, 0.9 mm or 1 mm or any non-integer value within said range of 0.1 to 1 mm.

In some embodiments, the prong heads snap-fit into place so as to secure the blocking cap onto the cervical plate. In some embodiments the blocking cap prong or prongs are flexible or elastically deformable, so that they bend when being forced through an interior opening or interior cavity of a cervical plate, and return to their original configuration when they pass through the interior opening or interior cavity until they reach a space having a width that allow the prongs to return to an undeformed position. In some embodiments, the prongs are made of the same material as the rest of the blocking cap. In some embodiments, the prongs are made of a material more flexible than the rest of the blocking cap. In some embodiments returning the prongs to an undeformed position secures the blocking cap in place. In some embodiments, the prongs can flex 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees or more from their original position or any non-integer value within said range of 1 to 15 degrees.

In some embodiments, the blocking cap has a size and shape to allow it to secure to the cervical plate and cover at least in part the screw holes of the cervical plate. In some embodiments, the blocking cap is round. In alternate aspects, the blocking cap is square or rectangular. In some embodiments, the corners of a square or rectangular blocking cap are rounded. In some embodiments, the blocking cap is 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm or 25 mm in diameter, or any non-integer value between 1 and 25 mm.

In some embodiments, a blocking cap comprises a cap surface that overlaps with at least one screw opening. In some embodiments a blocking cap comprises a cap surface that overlaps all of the screw openings, such that when a screw is threaded through a screw opening and a blocking cap is secured to the cervical plate, for example through a cervical plate opening, the cap surface overlaps the screw opening and prevents a screw, such as a loosened screw, from disengaging from the cervical plate. In some embodiments, the blocking cap covers 10% of the surface of the screw. In some embodiments, the blocking cap covers 100% of the surface of the screw. In some embodiments, the blocking cap covers 10-20%, 20-30%, 30-40%, 40-50%, 50-60%, 60-70%, 70-80%, 80-90%, 91%, 92%, 93%, 94%, 95%, 96% 97%, 98%, 99% of the surface of the screw or any integer or non-integer value within said range of 10 to 100%.

In some embodiments, the cervical plate comprises a material selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). [Are there additional materials that the cervical plate could be made from?] In some embodiments, the cervical plate and blocking cap are made by injection molding. In some embodiments, the cervical plate and blocking cap are made by machine.

In some embodiments, the cervical plate is provided in a sterile package, such as a singly sealed or doubly sealed sterile package. In some embodiments, the cervical plate is provided together with the blocking cap and bone screws, packaged together or separately in an unassembled configuration. In alternate embodiments the cervical plate is provided with a blocking cap and additionally with a cervical implant such as the cervical implant depicted herein, packaged separately or together in singly or doubly-enclosed sterile packaging. In alternate embodiments the cervical plate is provided with a blocking cap and additionally with a cervical implant such as the cervical implant depicted herein, and additionally packaged with a cervical implant delivery device packaged separately or together in singly or doubly-enclosed sterile packaging. In certain embodiments, the cervical plate is provided with a blocking cap and additionally with a cervical implant such as the cervical implant depicted herein, and additionally packaged with a cervical implant delivery device that is fabricated by a molding procedure for disposal after a single use, packaged separately or together in singly or doubly-enclosed sterile packaging. In certain embodiments, the cervical plate prongs are configured to interface compatibly with a cervical implant cavity that also releasably or reversibly interfaces with a cervical implant insertion device, such as a single use, molded, disposable cervical implant insertion device. That is, in some embodiments the cervical plate and blocking cap are components of a system that comprises a cervical implant and a cervical implant delivery device, such that elements of the cervical implant, cervical plate, and cervical implant insertion device are configured for coordinate use, for example by configuring the cervical plate prongs and the cervical implant insertion device such that each independently compatibly interfaces with the cervical implant cavity. In some embodiments, the components described herein are provided in a kit with instructions for use.

As described herein, a cervical implant is an implant inserted into an intervertebral space, such as between any two adjacent or consecutive vertebrae of a human spinal column, for example consecutive vertebrae that are intended to be fused or otherwise secured to restrict their movement relative to one another. In some embodiments, the cervical implant and cervical plate are deployed in alternate locations between two non-vertebral bone fragments that are to be secured or fused, such that In some embodiments the cervical plate is used to secure an insert in a location in a human other than an intervertebral space. Nonhuman cervical plates are also contemplated herein, such as cervical plates for nonhuman mammalian use such a veterinary use or other animal use.

Provided herein are methods of securing a cervical implant into a patient comprising use of the cervical plate described herein. Also provided herein is a method of securing a cervical plate into a patient comprising use of the cervical plate described herein. In some embodiments, a blocking cap prevents one or more screws from disengaging from the cervical plate. In some embodiments, the patient has a spinal injury, degenerative spinal condition, or spinal deformity and is receiving treatment for such. In some embodiments, the patient is undergoing spinal fusion surgery. In some embodiments, the patient is a mammal. In some embodiments, the patient is a cat, dog, rabbit, horse or other companion animal. In some embodiments, the patient is a human.

FIG. 1 shows an anterior view of an embodiment of a cervical plate 100. In some embodiments, the cervical plate 100 comprises four essentially circular screw holes 120*a*, 120*b*, 120*c*, and 120*d*. As shown in FIG. 1, in some embodiments, a cervical plate 100 may be substantially square in shape with rounded corners and slightly indented sides. A cervical plate 100 may be essentially any shape, for example, a cervical plate may be essentially circular, for example, a cervical plate may be essentially triangular in shape, for example, a cervical plate may be essentially elliptical in shape. In some embodiments, the cervical plate 100 comprises three essentially circular screw holes 120*a*, 120*b*, 120*c*. In some embodiments, the cervical plate 100 comprises two essentially circular screw holes 120*a*, 120*b*. In some embodiments, the cervical plate 100 comprises one essentially circular screw hole 120*a*. In the embodiment shown in FIG. 1, four screw holes 120*a*, 120*b*, 120*c*, and 120*d* are each respectively positioned essentially at a corner of the cervical plate 100. In some embodiments, a screw hole may be any shape and in any position on the surface of the cervical plate 100. For example, in some embodiments, a cervical plate 100 comprises two screw holes 120*a*, and 120*b* that are each positioned at a midway point along a length of one side of the cervical plate 100. In some embodiments, a cervical plate 100 comprises a coupler 130 that is configured to couple the cervical plate 100 to a cervical implant (not shown in FIG. 1). In some embodiments, cervical plate coupler 130 comprises one or more prongs. In some embodiments, a cervical plate coupler 130 comprises four prongs. In some embodiments, a cervical plate coupler 130 comprises three prongs. In some embodiments, a cervical plate coupler 130 comprises two prongs as shown in FIG. 1. In some embodiments, a cervical plate coupler 130 comprises one prong. In some embodiments, one or more prongs may be positioned at approximately the center of the cervical plate 100. In some embodiments, one or more prongs may be positioned so that the one or more prongs are essentially perpendicular to the cervical plate 100. In some embodiments, a cervical plate coupler 130 may comprise one or more openings for respectively receiving one or more prongs on a cervical implant to facilitate coupling of the cervical implant to the cervical plate 100. In some embodiments, one or more openings on the cervical plate 100 are positioned at approximately the center of the cervical plate 100. In some embodiments, a cervical plate coupler 130 may comprise a threaded component for threadably coupling to a threaded component on a cervical implant. In some embodiments, a cervical plate coupler 130 is configured to couple with a cervical implant by a snap-fit coupling. In some embodiments, a snap-fit coupling comprises any mechanism wherein a user may couple a cervical plate 100 to a cervical implant by manually pressing the two components together. In some embodiments, a cervical plate 100 comprises a central opening 140. In some embodiments, a central opening 140 is configured to receive a blocking cap coupler (not shown). One or more of the holes 120a, 120b, 120c, and 120d comprise a cut-out 160 that comprises an indentation in the surface of the cervical plate 100 that is configured to receive at least a portion of the blocking cap. That is, in this embodiment, the cervical plate 100 further comprises one or more cut outs 160 that comprise indentations that are configured to seat one or more portions of the blocking cap so that the one or more portions of the blocking cap are seated at least partially over the screw holes 120a, 120b, 120c, and 120d when the blocking cap is coupled with the cervical plate 100.

Figure 2:
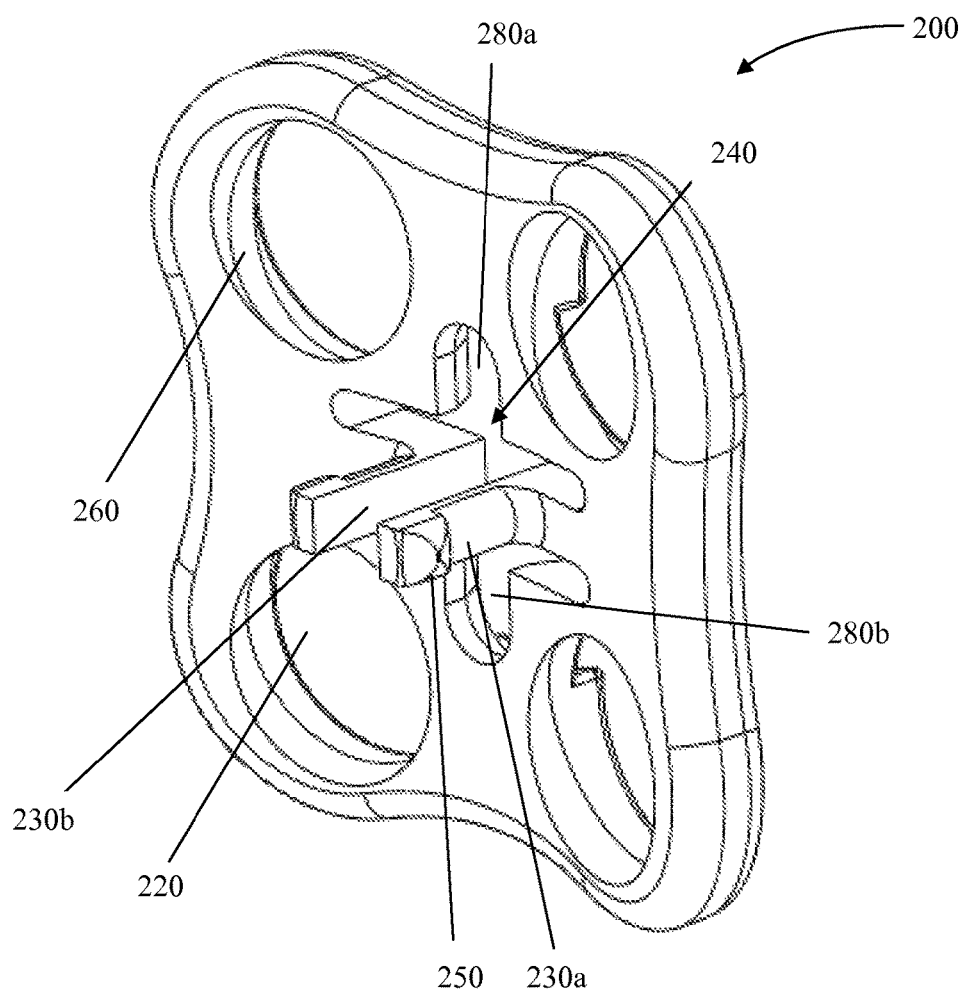
FIG. 2 shows a posterior view of an embodiment of a cervical plate.

FIG. 2 shows a posterior view of an embodiment of a cervical plate 200. In some embodiments, a central hole 240 comprises two recesses 280a and 280b that are configured to receive one or more blocking cap couplers (not shown). In some embodiments, a blocking cap coupler comprises one or more prongs or protrusions that snap fit to recesses 280a and 280b. In some embodiments, a cervical plate 200 comprises one or more prongs. In some embodiments, a cervical plate 200 comprises prongs 230a and 230b that are positioned essentially perpendicular to and substantially centrally positioned on said cervical plate 200. In some embodiments, one or more prongs comprises a prong head 250 that comprises protrusions or ridges that are configured to securely snap fit a coupler on a cervical implant body (not shown). In some embodiments, one or more of the screw holes 220 comprises a threaded inner surface 260. In some embodiments, a threaded inner surface 260 is configured to threadably couple with a screw. In some embodiments, one or more the screw holes 220 are not threaded. In some embodiments, the screw holes 220 comprise an angled interior rim or edge 260, wherein the angled interior rim 26 is configured to seat a received screw that passes through the screw hole 220 at an angle. In some embodiments, the rim or edge 260 comprises a complete circular or ovoid shape. In some embodiments, the rim or edge 260 comprises only a partial circular or ovoid shape. In some embodiments, one or more of the screw holes 220 comprise a first opening on the external surface of the cervical plate and a second opening on the internal surface of the cervical plate, and the diameter of the first opening is larger than the second opening. In this embodiment, the diameter of the first opening which is positioned on the external surface of the cervical plate is wider than a screw head of a screw used to secure the cervical plate to the cervical vertebra. In this embodiment, the diameter of the second opening on the internal surface is smaller than the diameter of a screw head of a screw used to secure the cervical plate to the cervical vertebra. In some embodiments, a smaller in diameter second opening is positioned so that it is slightly offset from the center of the larger in diameter first opening, thereby forming interior rim or edge 260 which comprises the offset outer edge of the second smaller in diameter opening. This embodiment, allows a screw to be positioned at different angles as it is passed through the screw holes of the device, wherein the larger in diameter first opening allows for different positions of the screw relative to the device, and the edge 260 created by the smaller second opening secures the screw by engaging the screw head within the screw hole 220.

Figure 3:
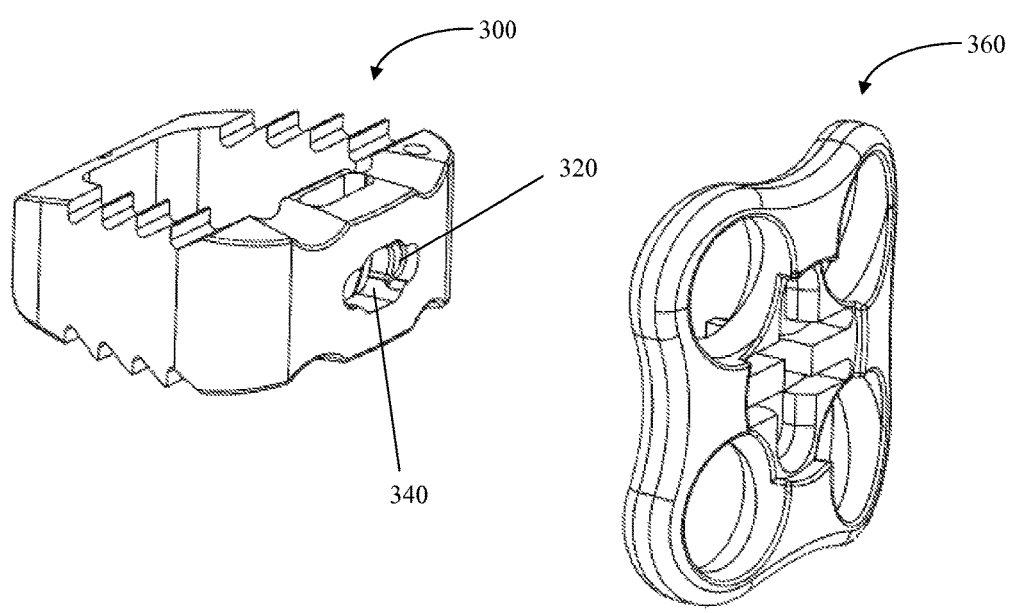
FIG. 3 shows an embodiment of a cervical implant together with an embodiment of a cervical plate, wherein the cervical implant and the cervical plate are not coupled.

FIG. 3 shows an embodiment of a cervical implant 300 together with an embodiment of a cervical plate 360, wherein the cervical implant 300 and the cervical plate 360 are not coupled. In some embodiments, a cervical implant comprises a cervical implant coupler 340 that is configured to couple with a cervical plate coupler (not shown). In some embodiments, the cervical implant coupler 340 comprises an opening that is configured to receive a cervical plate coupler. In some embodiments, the cervical implant coupler 340 comprises an opening and further comprises one or more edges 320 that protrude into the opening, wherein the one or more edges 320 are configured to engage one or more engagers on the cervical plate coupler. In some embodiments, a cervical plate coupler comprises one or more prong heads (see FIG. 2) which act as engagers for engaging with the one or more edges 320. In some embodiments, the prong heads are protrusions that engage with the one or more engages 320 on the cervical implant so that the cervical plate cannot be pulled back once coupled with the cervical implant. In some embodiments, the engagers 320 on the cervical implant 300 and the engagers on the cervical plate 360 facilitate snap-fit coupling, so that a user can manually couple the two elements together by pressing them together.

Figure 4:
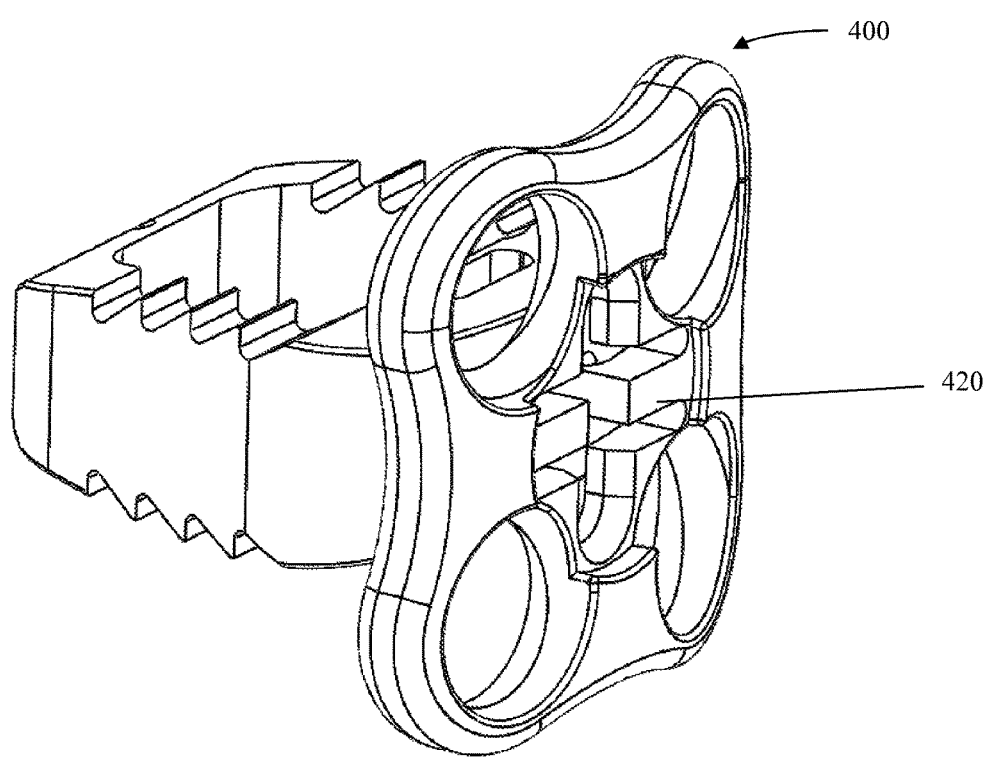
FIG. 4 shows an embodiment of a coupled cervical implant and cervical plate.

FIG. 4 shows an embodiment of a coupled cervical implant and cervical plate 400. In some embodiments, the cervical implant and cervical plate reversibly couple. In some embodiments, the cervical implant and the cervical plate are not configured to reversibly couple, and the coupling forms a permanent coupling. In some embodiments, the cervical implant and cervical plate are configured to snap-fit together as described herein.

Figure 5:
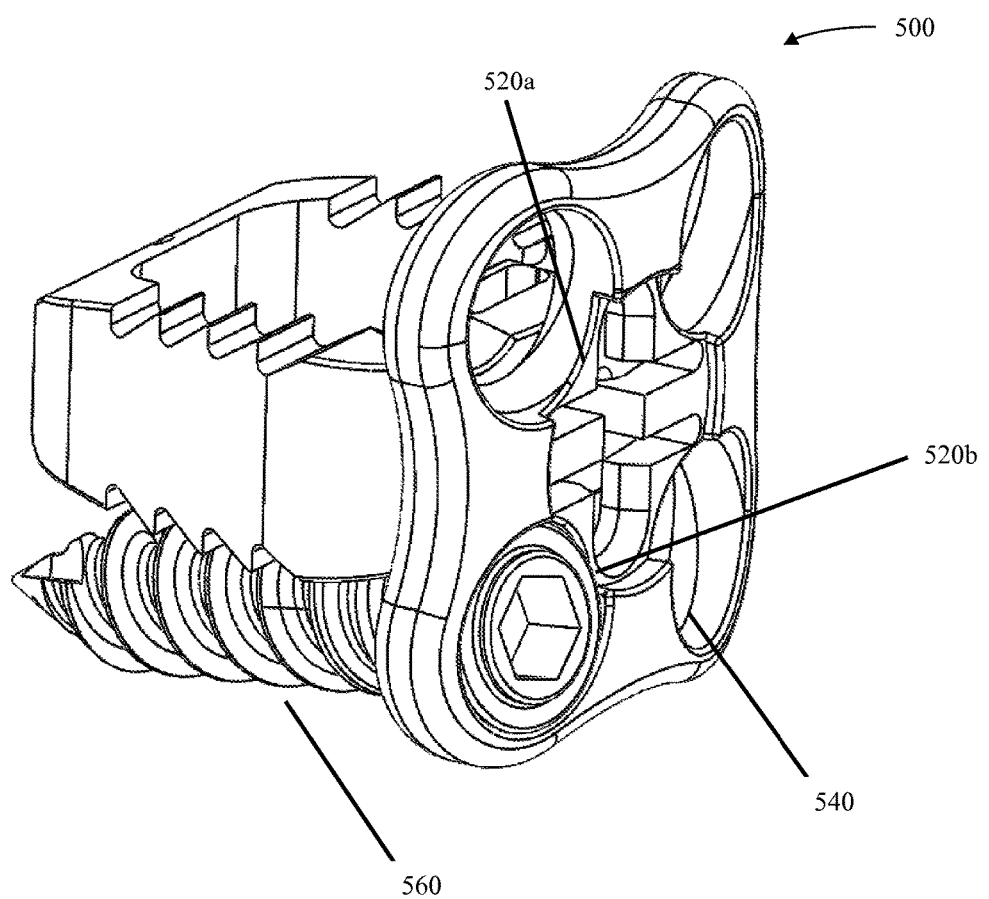
FIG. 5 shows an embodiment of a coupled cervical implant and cervical plate with a screw.

FIG. 5 shows an embodiment of a coupled cervical implant and cervical plate 500 with a screw 560. In some embodiments, screw 560 is seated at an angle within a hole on the cervical plate. In this embodiment, the angled seat in which the screw sits comprises an angled rim or edge 540 that is configured to seat screw 560 at an angle relative to the coupled cervical implant and cervical plate 500. In some embodiments, the cervical plate further comprises one or more cut outs 520a and 520b which are configured to receive a blocking cap so that the blocking cap (not shown) at least partially is positioned directly over one or more screws. In some embodiments, cut out 520b is configured to receive a portion of a blocking cap so that that blocking cap portion is positioned directly over screw 560. The direct positioning of the blocking cap over screw 560, when the blocking cap is coupled with the cervical plate, prevents screw 560 from backing out.

Figure 6:
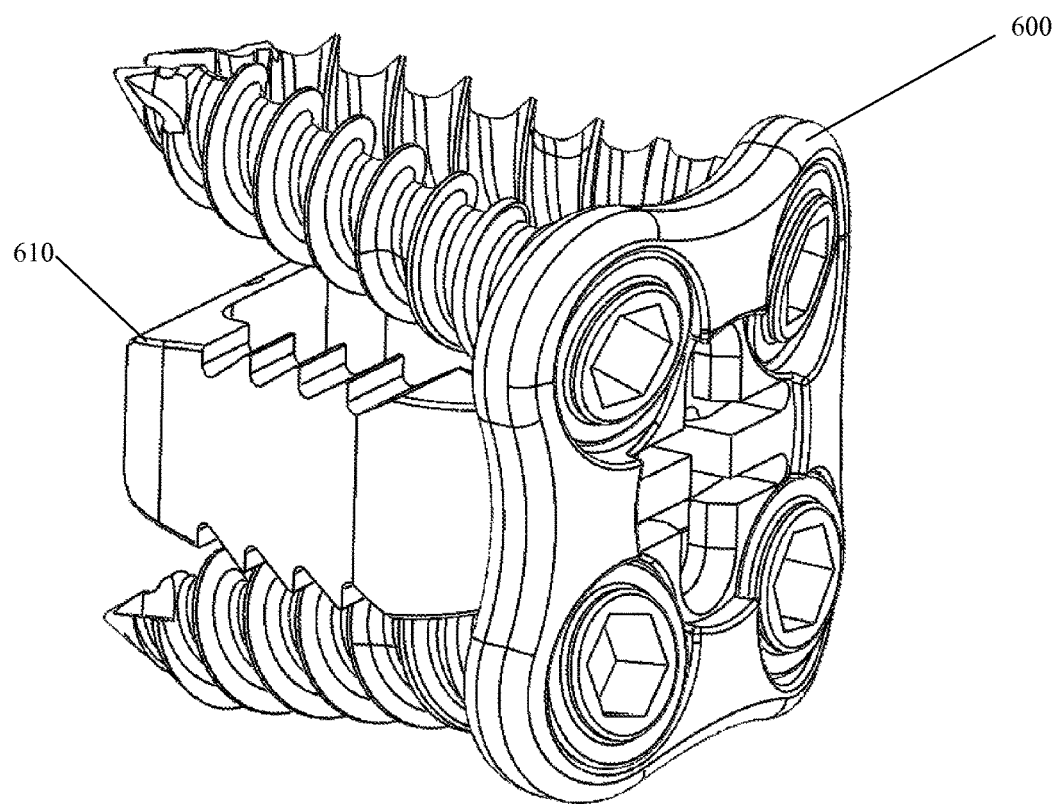
FIG. 6 shows an embodiment in which four screws are placed through four screw holes of a cervical plate which is coupled with a cervical implant.

FIG. 6 shows an embodiment of a cervical plate 600 in which four screws are placed through four screw holes coupled with a cervical implant 610. In this embodiment, the screws on opposite sides of the cervical insert are divergently positioned. As described, in some embodiments, cervical implant 610 and cervical plate 600 are configured to couple in a snap-fit fashion through complimentary snap-fit couplers, one snap-fit coupler on the implant and one snap-fit coupler on the cervical plate.

Figure 7:
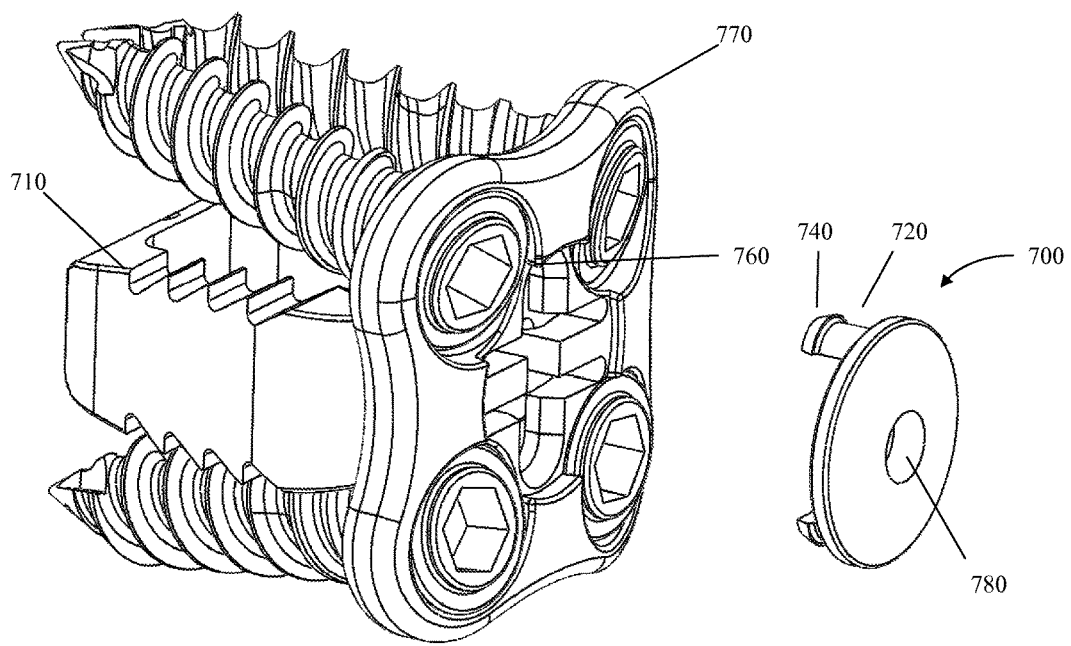
FIG. 7 shows an embodiment in which four screws are placed through four screw holes of a cervical plate which is coupled with a cervical implant shown next to an embodiment of a blocking cap.

FIG. 7 shows an embodiment of a cervical plate 770 through which four screws are placed through four screw holes, and wherein the cervical plate 770 is further coupled with a cervical implant 710. FIG. 7 further shows an embodiment of a blocking cap 700. In some embodiments, a blocking cap 700 comprises a blocking cap coupler 720 that is configured to couple a blocking cap 700 to a cervical plate 770, and in particular a cervical plate 770 that is coupled to an implant body 710, and through which are passed one or more screws, as shown. In some embodiments, a blocking cap coupler 720 comprises one or more prongs. In some embodiments, one or more prongs further comprise one or more blocking cap prong heads 740. A blocking cap prong head 740 may comprise a protrusion that is configured to engage an opening or indentation on a cervical plate 760. In some embodiments, the opening or indentation in the cervical plate 760 creates a passage from the anterior surface of the cervical implant through to the posterior surface of the cervical plate. In some embodiments, one or more blocking cap prong heads 740 are configured to respectively engage with one or more openings or indentations on a cervical plate so that when the two elements are pressed together, the one or more blocking cap heads 740 passes through the opening or indentation 760 on an anterior side of a cervical plate and snaps snugly against the posterior side of the cervical plate 770 so that the blocking cap 700 cannot be separated from the cervical plate by pulling (or pushing) the blocking cap 700 away from the cervical plate 770. In some embodiments, blocking cap 700 comprises an engager 780 for engaging and coupling with a delivery device (not shown in FIG. 7). An engager 780 may, for example, comprise a snap-fit connector for coupling with a delivery device, or, alternatively an engager 780 may, for example, comprise a threaded opening that threadably couples with said delivery device.

Figure 8:
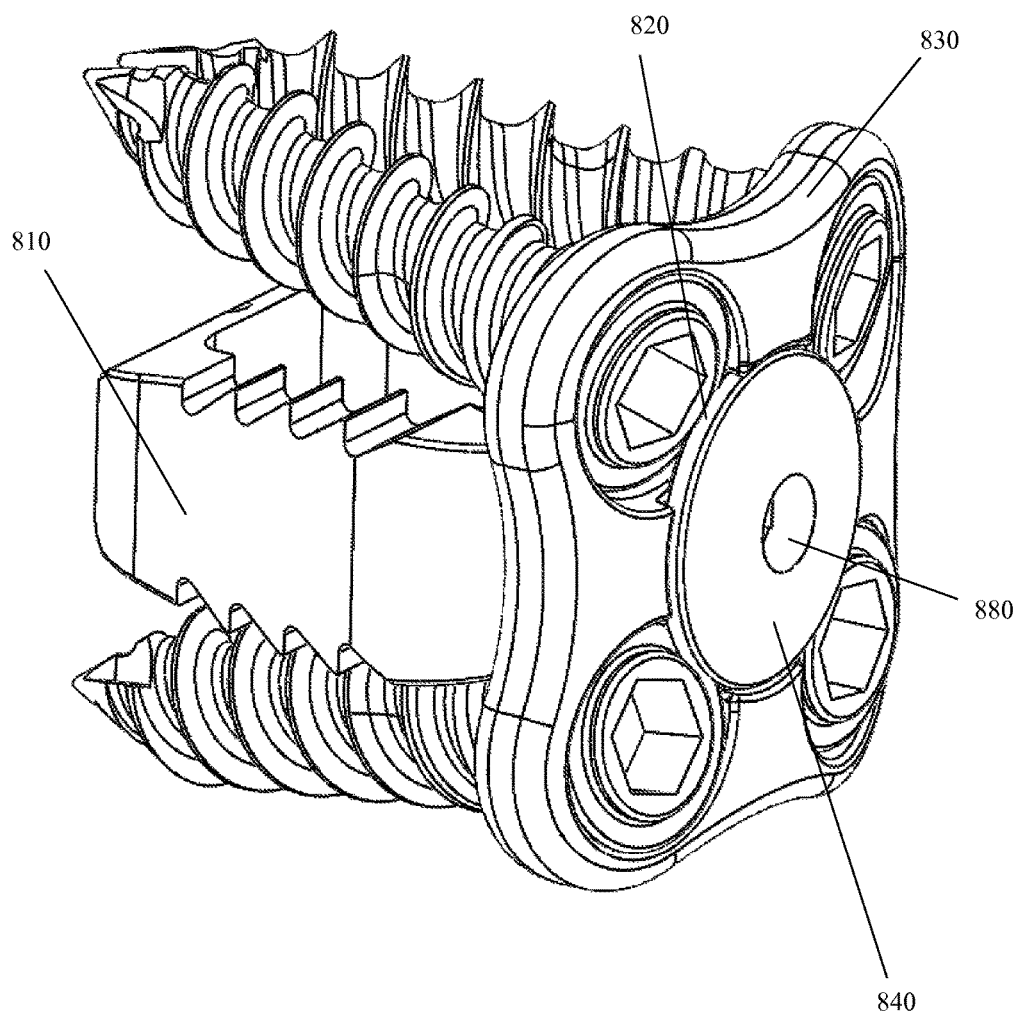
FIG. 8 shows an embodiment of a blocking cap coupled with an embodiment in which four screws are placed through four screw holes of a cervical plate which is coupled with a cervical implant.

FIG. 8 shows an embodiment of a blocking cap 840 coupled with an embodiment of a cervical plate 830 coupled with cervical implant 810, and wherein four screws are placed through four screw holes of the cervical plate 830. In some embodiments, one or more portions of an edge of a blocking cap 820 at least partially directly cover at least a portion of one or more screws. In some embodiments, the cervical implant 810 is positioned between two vertebra, the cervical plate 830 is coupled with the cervical implant 810, one or more screws are placed through the holes of the cervical plate 830 and into one or more of the vertebra between which the implant 810 is positioned, and a blocking cap 840 is coupled with a cervical plate so that the securely coupled blocking cap 840 prevents the one or more screws from backing out of the one or more vertebra. As described, in some embodiments, the blocking cap 840 is configured to couple with the cervical plate so that it is not displaced from the cervical plate by an outward directed force (i.e. either pushing or pulling of the blocking cap). In some embodiments, the cervical implant 810, the cervical plate 830, and the blocking cap 840 all couple together through a snap-fit mechanism, wherein the elements are configured so that a user may couple one or more of the elements to each other by manually pressing them together. In some embodiments, the blocking cap comprises an engager 880 for engaging and coupling with a delivery device (not shown in FIG. 8). An engager 880 may comprise a snap-fit connector for coupling with a delivery device, or, alternatively an engager 880 may comprise a threaded opening that threadably couples with said delivery device and delivers said blocking cap to a cervical plate so that said blocking cap may couple with said cervical plate as shown.

Figure 9:
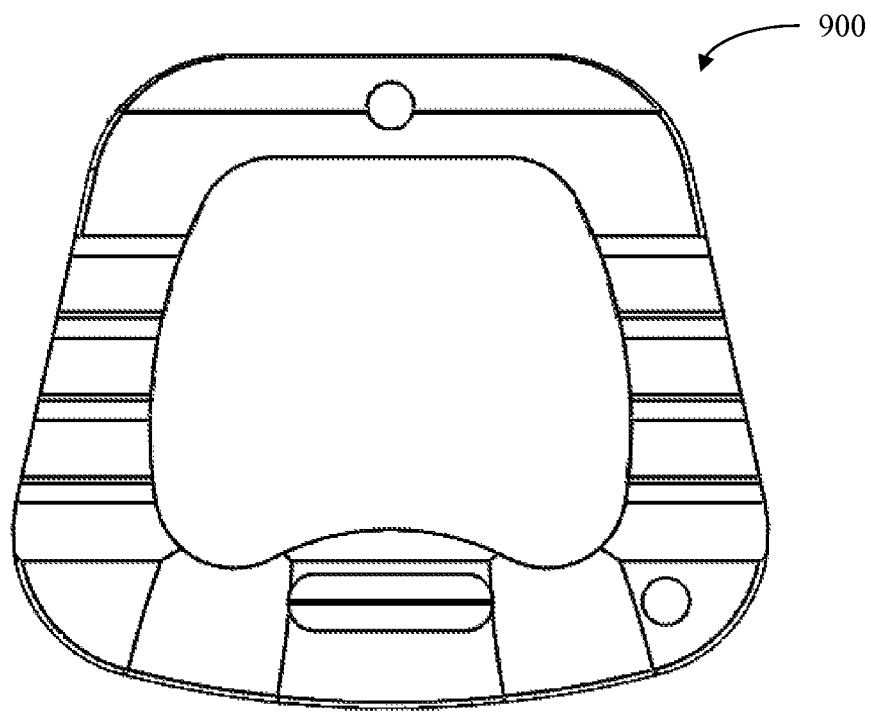
FIG. 9 shows an overhead view of an embodiment of a cervical plate positioned for engagement with a cervical implant.
Figure 9:
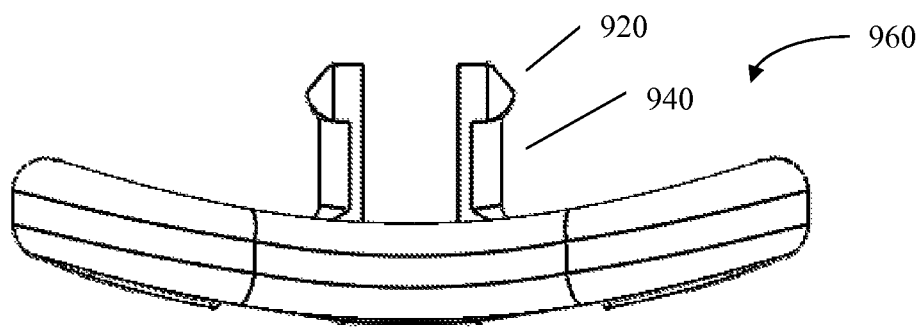

FIG. 9 shows an overhead view of an embodiment of a cervical plate 960 positioned for engagement with a cervical implant 900. In some embodiments, the cervical plate comprises prongs 940 having terminal prong heads 920.

Figure 10:
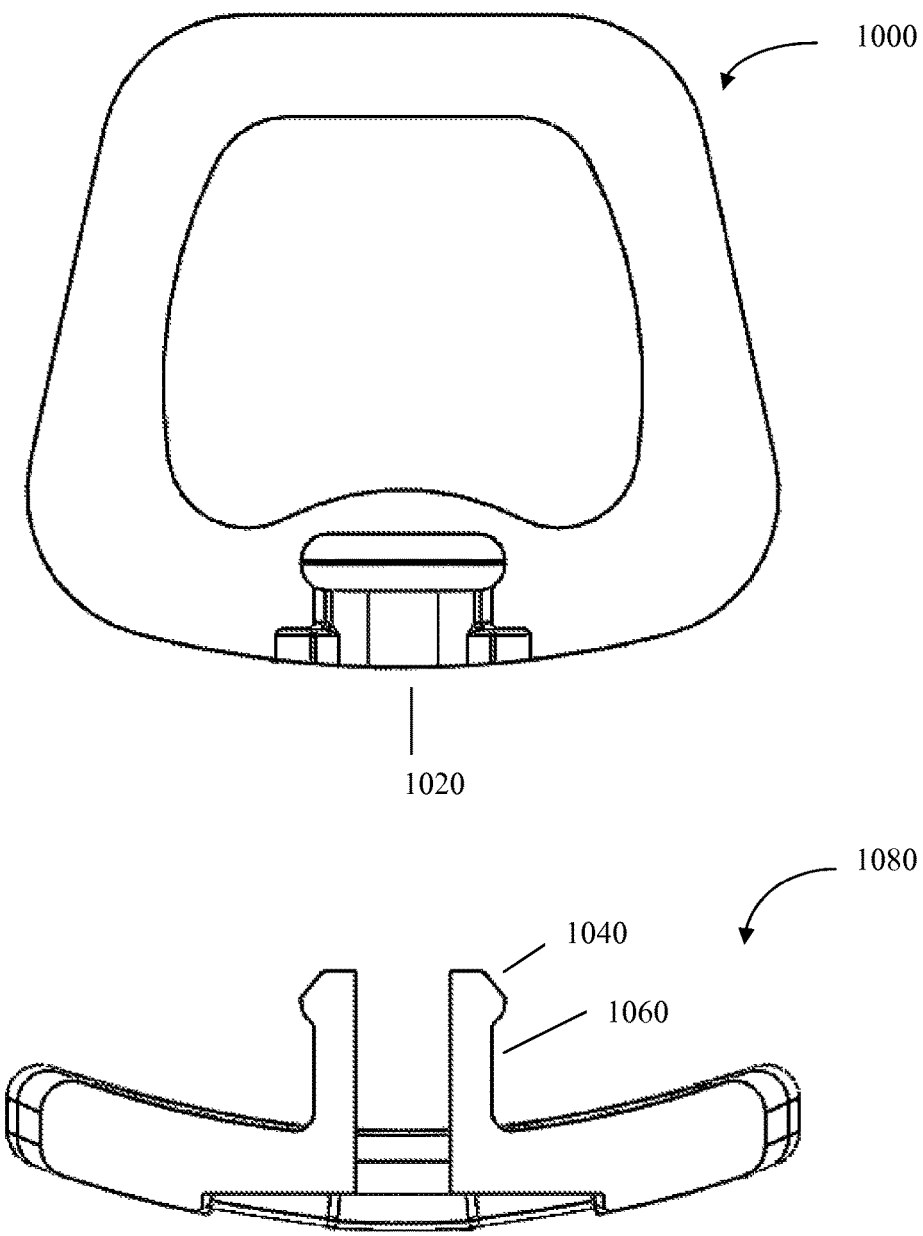
FIG. 10 shows a cross sectional view of an embodiment of the cervical plate together with the cervical implant, wherein the cervical plate and the cervical implant are not coupled.

FIG. 10 shows a cross sectional view of an embodiment of the cervical plate 1080 together with the cervical implant 1000, wherein the cervical plate 1080 and the cervical implant 1000 are not coupled. In some embodiments, the cervical implant coupler comprises cavity 1020, which is configured to receive and couple with a cervical plate coupler comprising one or more prongs 1060 on the cervical plate 1080. In the embodiment shown, the cervical plate coupler comprises two prongs 1060. In some embodiments, a prong 1060 comprises a prong head 1040. In the embodiment shown a prong head 1040 comprises a tapered protrusion at the end of the prong. The width of the cavity 1020 is configured to allow relatively easy passage of the one or more prongs of the cervical plate 1080 into the cavity during coupling. In some embodiments, a width of the cavity 1080 at its opening may be slightly less than the largest width of the prongs 1060 so that the cavity opening allows passage of the prongs 1060 by compressing the prongs 1060 together. In this embodiment, the cavity 1020 comprises a wider width in the space immediately behind the cavity opening so that once the prongs 1060 pass through the cavity opening the compressive force applied to the prongs 1060 no longer exist in the wider width space behind the cavity opening allowing the prongs 1060 to separate to their non-compressed width. In some embodiments, the separation of the prongs 1060 to their normal non-compressed width within the cavity 1020 generates a snap-like sound or sensation. In some embodiments, the one or more prong heads 1040 are configured to decrease the resistance to passage of the prongs 1060 through a cavity 1020 opening with a width that is smaller than the widest width of the prongs 1060. For example, in some embodiments, the prong heads 1060 are tapered, so that the maximum width of the prongs 1060 exists only at a single point, rather than over the entire length of the prong heads 1040 were they not tapered.

Figure 11:
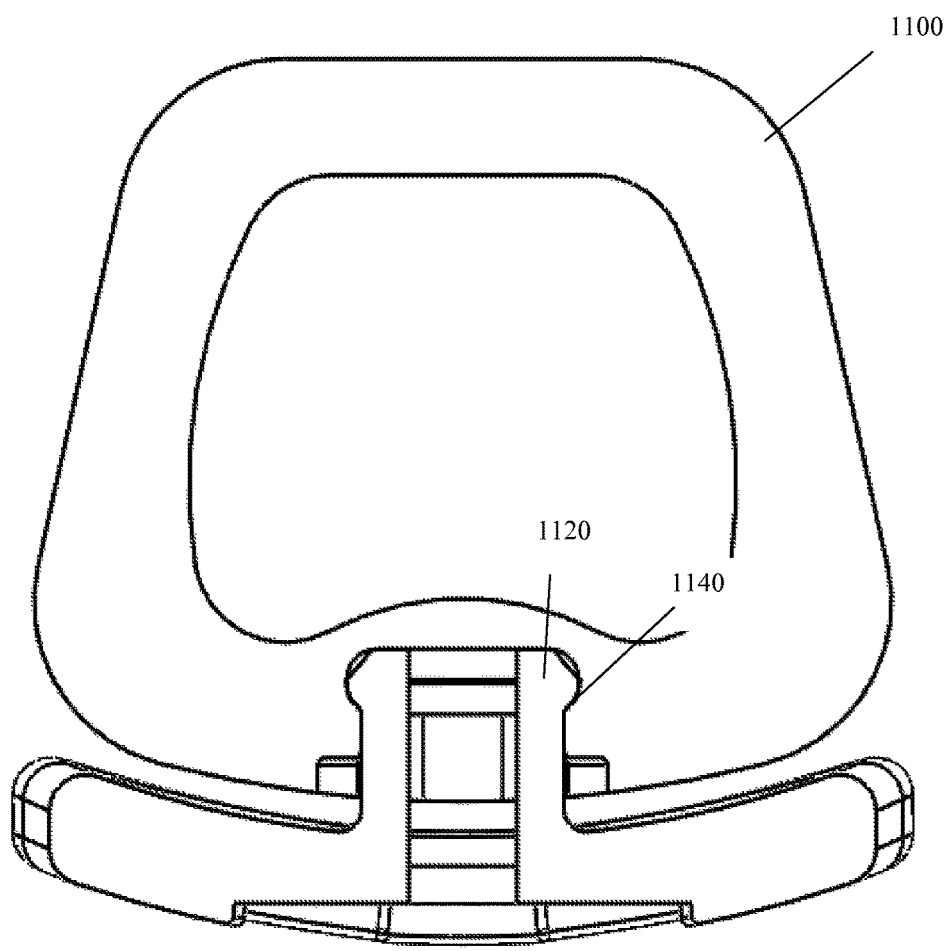
FIG. 11 shows a cross-sectional view of a cervical plate coupled with a cervical implant.

FIG. 11 shows a cross-sectional view of a cervical plate coupled with a cervical implant 1100. In some embodiments, one or more prong heads 1120 are configured to securely engage with an engager within the cavity of the cervical implant. In some embodiments, the engager within the cavity of the cervical implant comprises a protruding edge 1140 that has a width that is smaller than the widest width of the one or more prong heads 1120. In some embodiments, once the prong heads are advanced into the wider portion of the cavity, as described herein, the prongs separate to their normal width and thereby the prong heads 1120 are positioned to abut the protruding edge of the cavity 1140. Because the prong heads 1120 are wider in diameter than the protruding edge 1140, they abut in such a way that the protruding edge 1140 prevents the cervical plate from being de-coupled from the cervical implant due to an outwardly directed force (i.e. pulling or pushing on the cervical plate).

Figure 12:
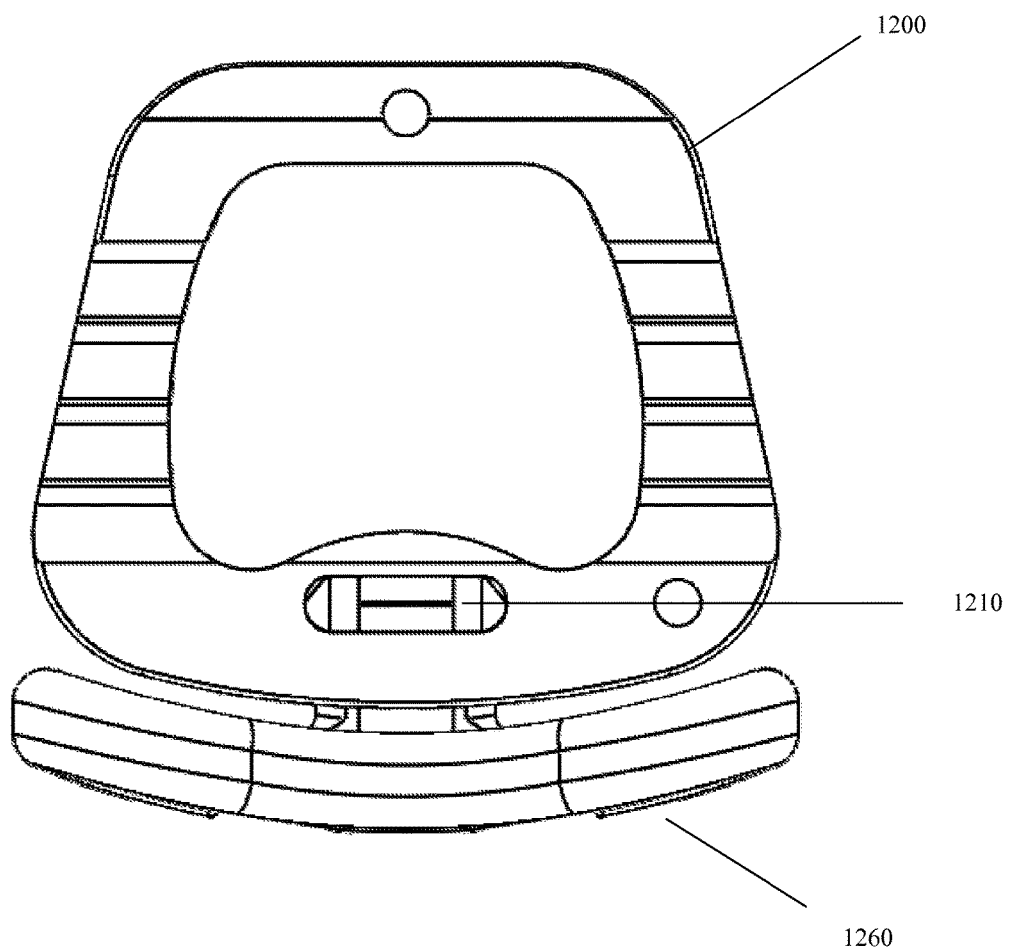
FIG. 12 shows a top view of an embodiment of a cervical plate engaged with a cervical cavity.

FIG. 12 shows a top view of an embodiment of a cervical plate 1260 engaged with a cervical implant 1200. A prong 1210 of the cervical plate 1260 is visible inside the cavity of the implant 1200, wherein the cavity comprises the coupler of the implant 1200 and the prong 1210 comprises part of the coupler of the cervical plate 1260.

Figure 13:
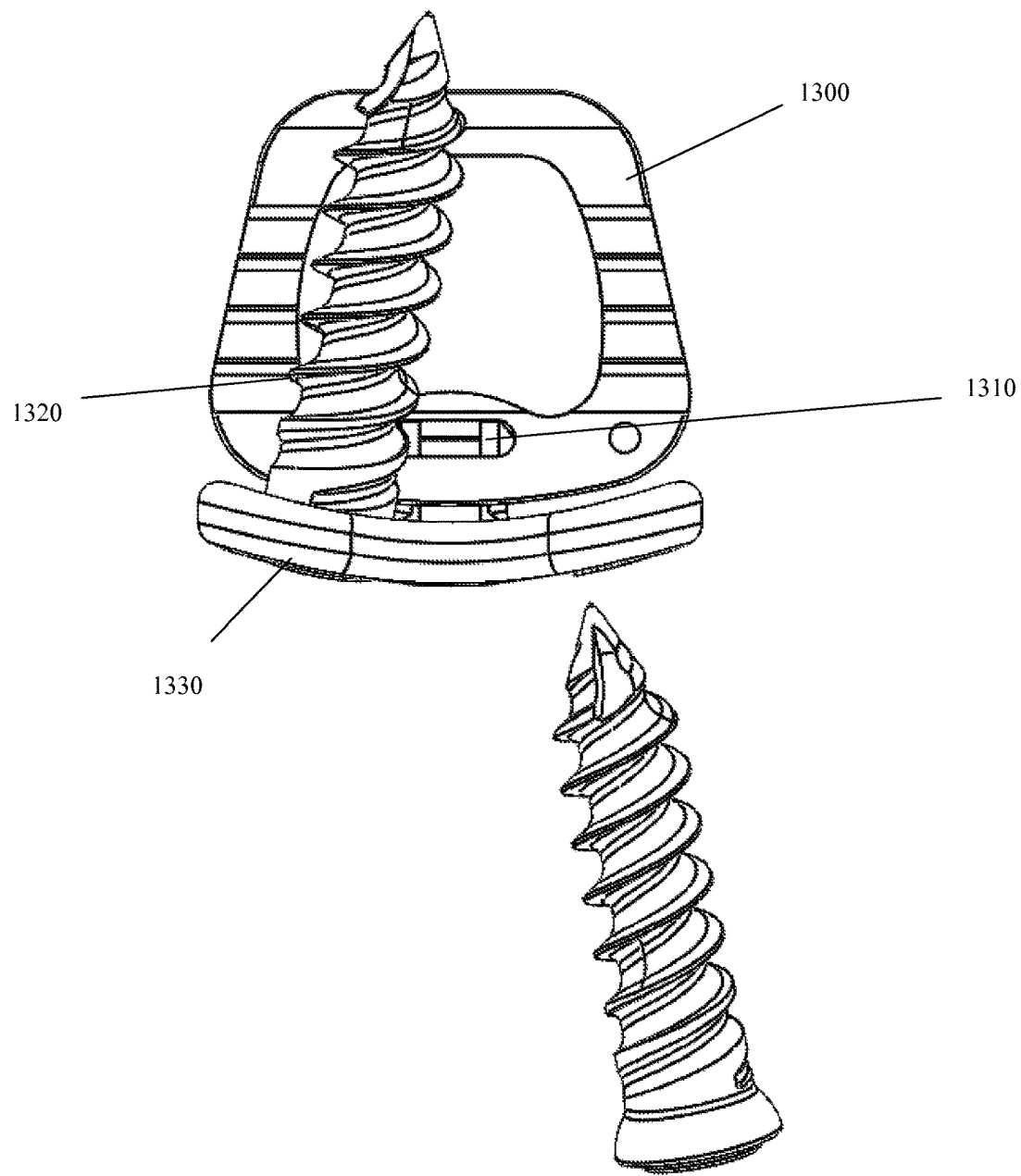
FIG. 13 shows a first screw engaged through a first screw hole of a cervical plate 1330, and a second screw positioned to be engaged in a second screw hole of the cervical plate, and wherein the cervical plate 1330 is coupled with an implant.

FIG. 13 shows a first screw 1320 engaged through a first screw hole of a cervical plate 1330, and a second screw positioned to be engaged in a second screw hole of the cervical plate, and wherein the cervical plate 1330 is coupled with an implant 1300. The first screw hole of the cervical plate 1330 is configured so that first screw 1320 is seated above the cervical implant 1300 when the first screw 1320 passes through the first screw hole of the cervical plate 1330 and the cervical plate 1330 and the implant 1300 are coupled.

Figure 14:
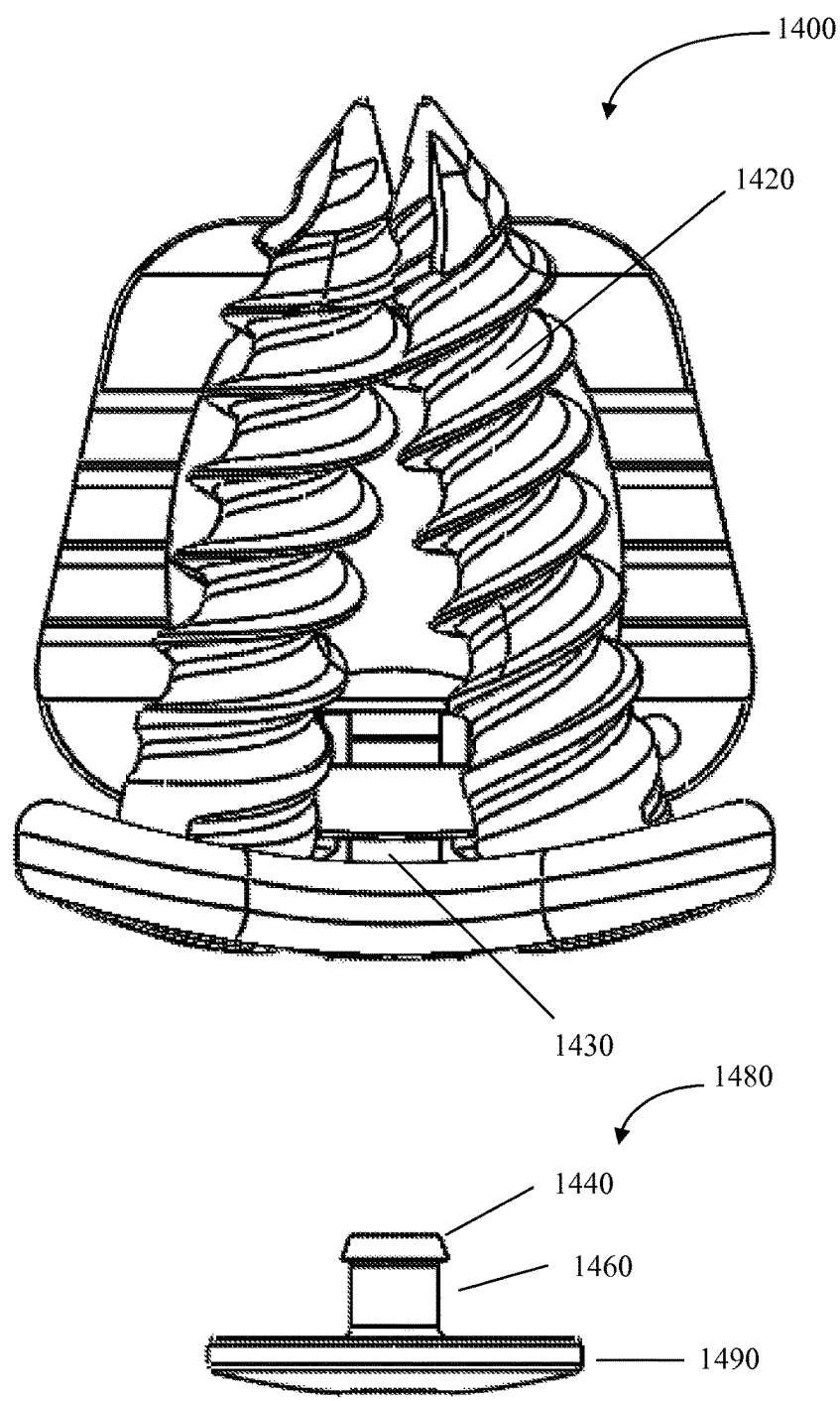
FIG. 14 shows a top view of an embodiment of a cervical implant coupled with a cervical plate 1400 through which are passed screws, along with an embodiment of a blocking cap that is not coupled with the cervical plate and cervical implant.

FIG. 14 shows a top view of an embodiment of a cervical implant coupled with a cervical plate 1400 through which are passed screws 1420, along with an embodiment of a blocking cap 1480 that is not coupled with the cervical plate and cervical implant. In some embodiments, a blocking cap 1480 is configured to snap-fit to a cervical plate coupled with a cervical implant 1400 through which screws were placed in order to prevent the screws from backing out. In some embodiments, the cervical plate and cervical implant are separate elements configured to couple together as described herein. In some embodiments, the cervical plate and cervical implant comprise a single unit that is manufactured as a single element. In some embodiments a blocking cap 1480 comprises an essentially circular plate 1490. In some embodiments, the blocking cap 1480 comprises a blocking cap coupler that is configured to couple the blocking cap 1480 with the cervical plate. In some embodiments, the blocking cap coupler comprises one or more prongs 1460. In some embodiments, one or more prongs comprise a blocking cap prong head 1440. In some embodiments, a blocking cap prong head 1440 comprises one or more protrusions. In some embodiments, the one or more protrusions are tapered. In some embodiments, as shown in FIG. 14, a blocking cap 1480 comprises a single prong 1460 positioned essentially in the center of the blocking cap 1480 along with a single blocking cap protrusion 1440 that is tapered and extends around the circumference of the prong. As described herein, a blocking cap prong 1460 is configured to advance through a first surface of a cervical plate to a second surface through an opening the cervical plate, and engage an edge along the cervical plate opening so that the blocking cap prong head 1440 locks into place and resists separation from the cervical plate to which it is coupled. In some embodiments, as shown in FIG. 14, the cervical plate is curved creating a small space 1430 between the coupled cervical plate and cervical implant 1400. In some embodiments, the blocking cap prong head 1440 is configured to substantially fit into a space 1430 between a coupled cervical implant and a cervical plate 1400 that is created by a curve in the cervical plate body.

Figure 15:
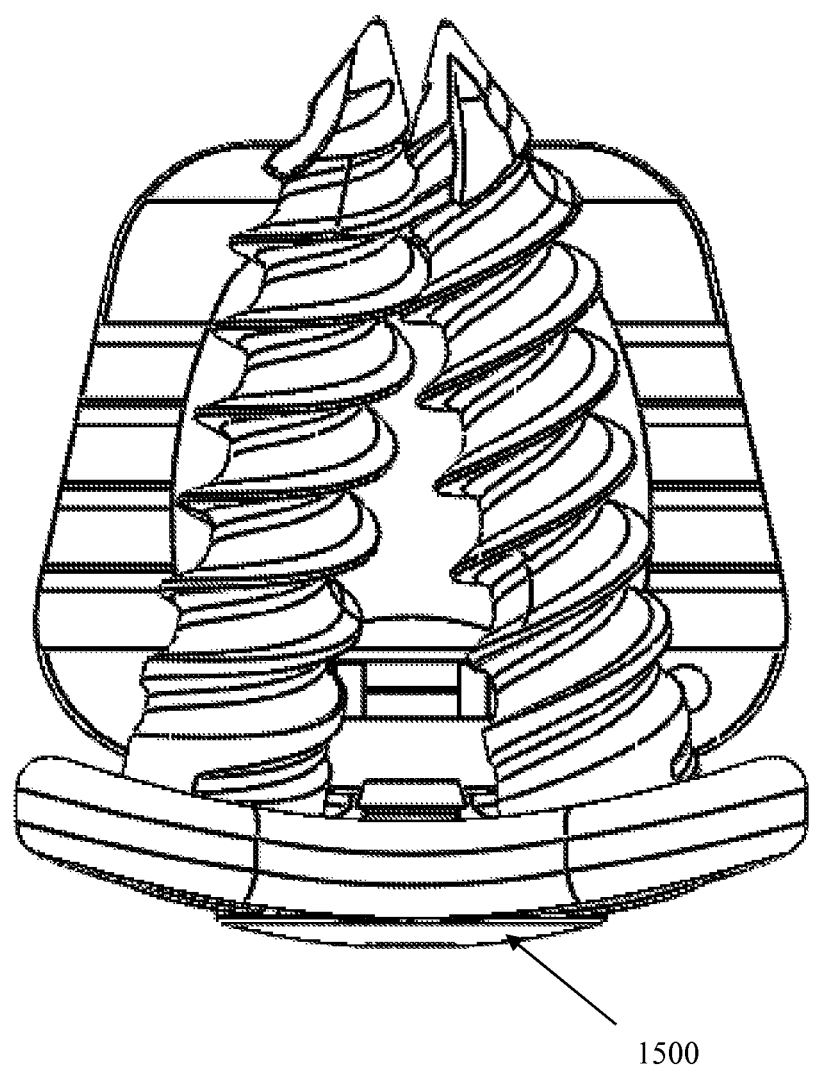
FIG. 15 shows an embodiment of a cervical cap coupled with a cervical plate, wherein the cervical plate is coupled with a cervical implant and screws are passed through the cervical plate as described herein.

FIG. 15 shows an embodiment of a cervical cap coupled with a cervical plate, wherein the cervical plate is coupled with a cervical implant and screws are passed through the cervical plate as described herein.

Figure 16:
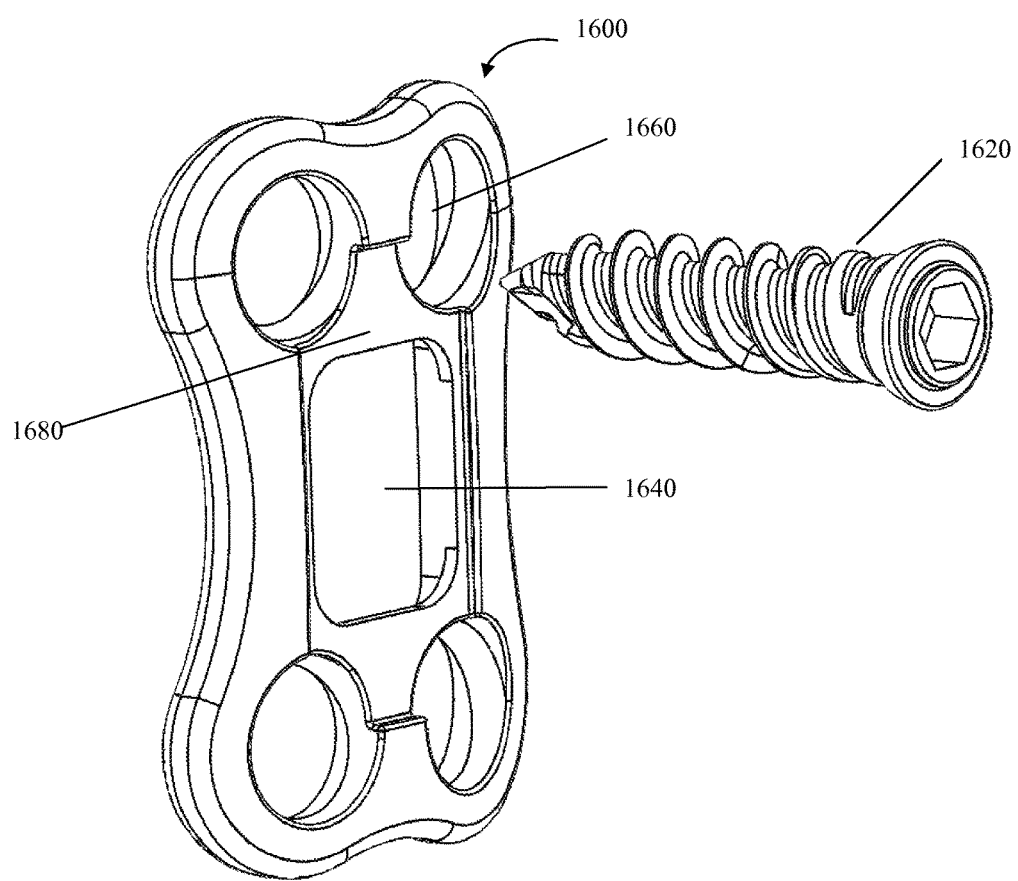
FIG. 16 shows an embodiment of a cervical plate.

FIG. 16 shows an embodiment of a cervical plate 1600. In some embodiments, a cervical plate 1600 is configured to be secured with one or more screws 1620 to one or more vertebrae. In some embodiments, a cervical plate comprises one or more screw holes 1660 that are configured to receive a screw 1620. In some embodiments, a cervical plate 1600 comprises a central opening 1640 configured to receive a blocking cap (not shown). In some embodiments, the cervical plate 1600 further comprises one or more cut outs 1680 positioned so that at least a portion of a blocking cap will be positioned directly over one or more screws respectively passed through one or more holes 166 when the blocking cap is coupled with the cervical plate 1600.

Figure 17:
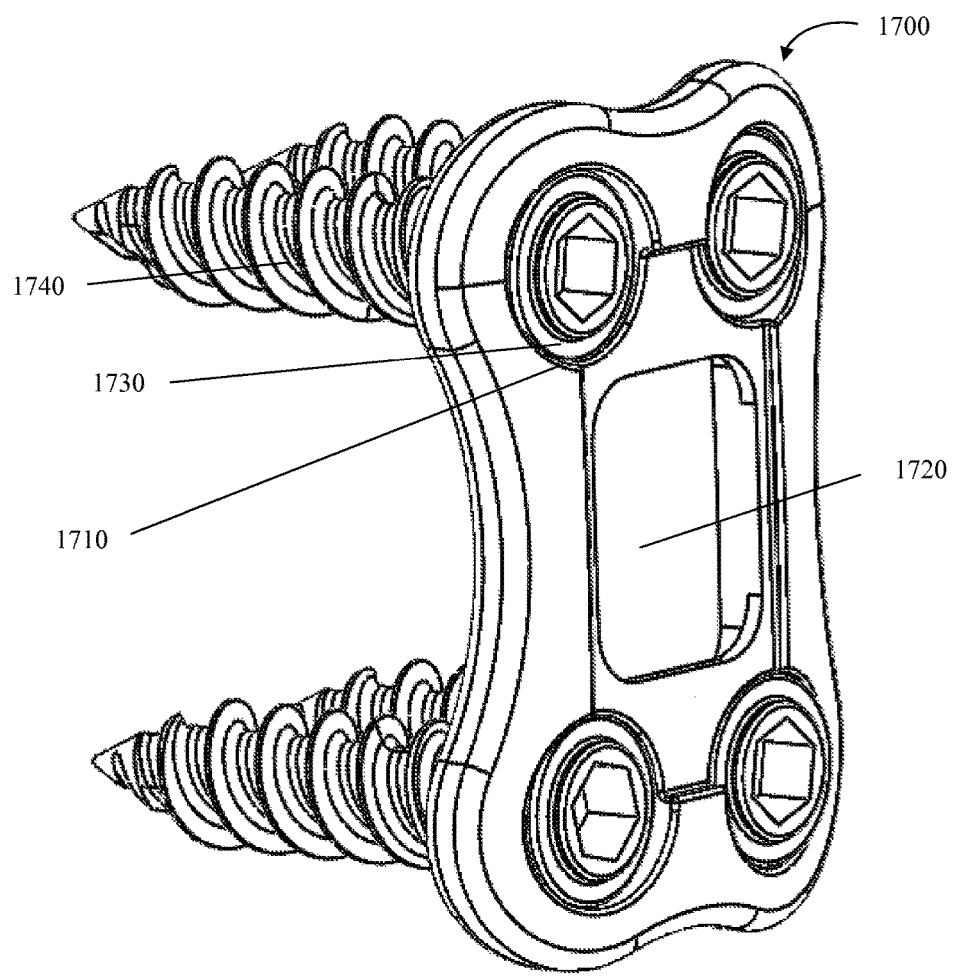
FIG. 17 shows four screws each passing through one of four screw holes.

FIG. 17 shows four screws each passing through one of the four screw holes. Indentation 1710 is positioned so that screw head 1730 will be seated essentially flush with the indentation 1710 of the cervical plate 1700 when screw 1740 is passed through cervical plate 1700. When a blocking cap (not shown) is coupled with the cervical plate 1700, a portion of the blocking cap fits essentially flush with indentation 1710 so that the blocking cap is flush with the screw head 1730 and prevents surgical screw 1740 from backing out of the screw hole in the cervical plate 1700.

Figure 18:
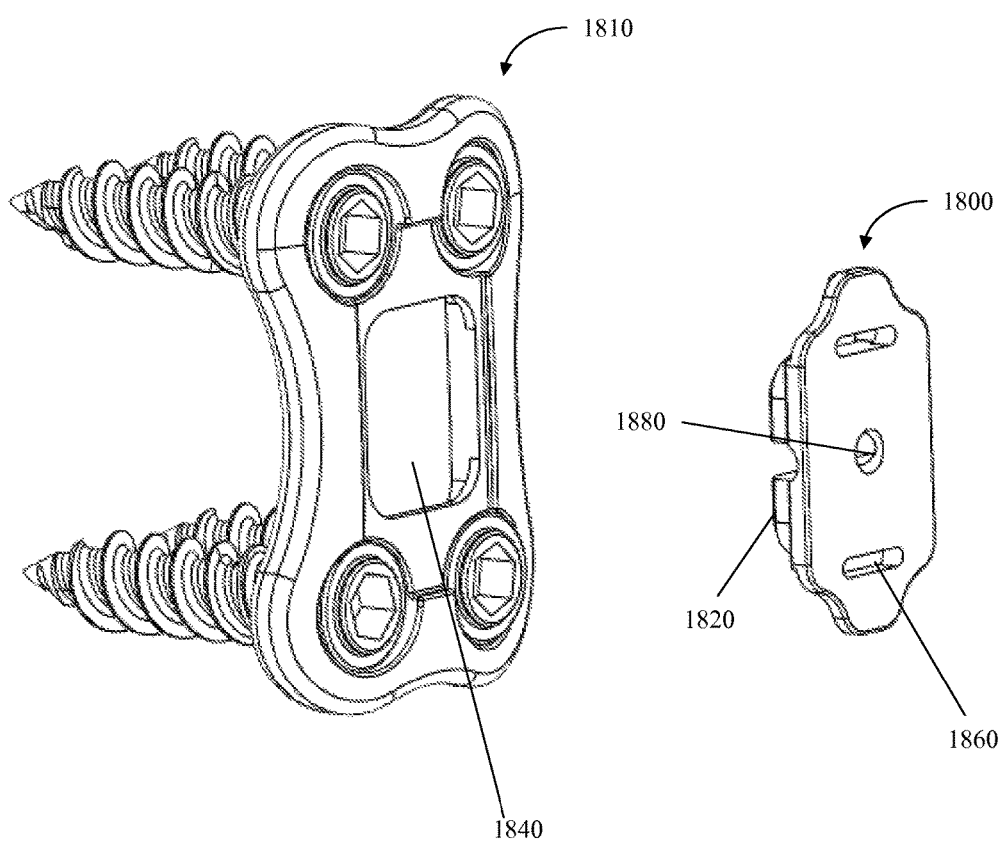
FIG. 18 shows an embodiment of a blocking cap coupled with an embodiment of a cervical plate through which are passing four screws.

FIG. 18 shows an embodiment of a cervical plate 1810 together with an embodiment of a blocking cap 1800, wherein the blocking cap 1800 is not coupled with the cervical plate 1810. In some embodiments, the cervical plate 1810 comprises a cervical plate coupler 1840 that is configured to couple with a blocking cap coupler 1820. In some embodiments, the cervical plate coupler 1840 comprises an opening configured to receive and seat a blocking cap 1800. In some embodiments, blocking cap 1800 comprises an engager 1880 for engaging and coupling with a delivery device (not shown in FIG. 18). An engager 1880 may comprise a snap-fit connector for coupling with a delivery device, or, alternatively an engager 1880 may comprise a threaded opening that threadably couples with said delivery device.

Figure 19:
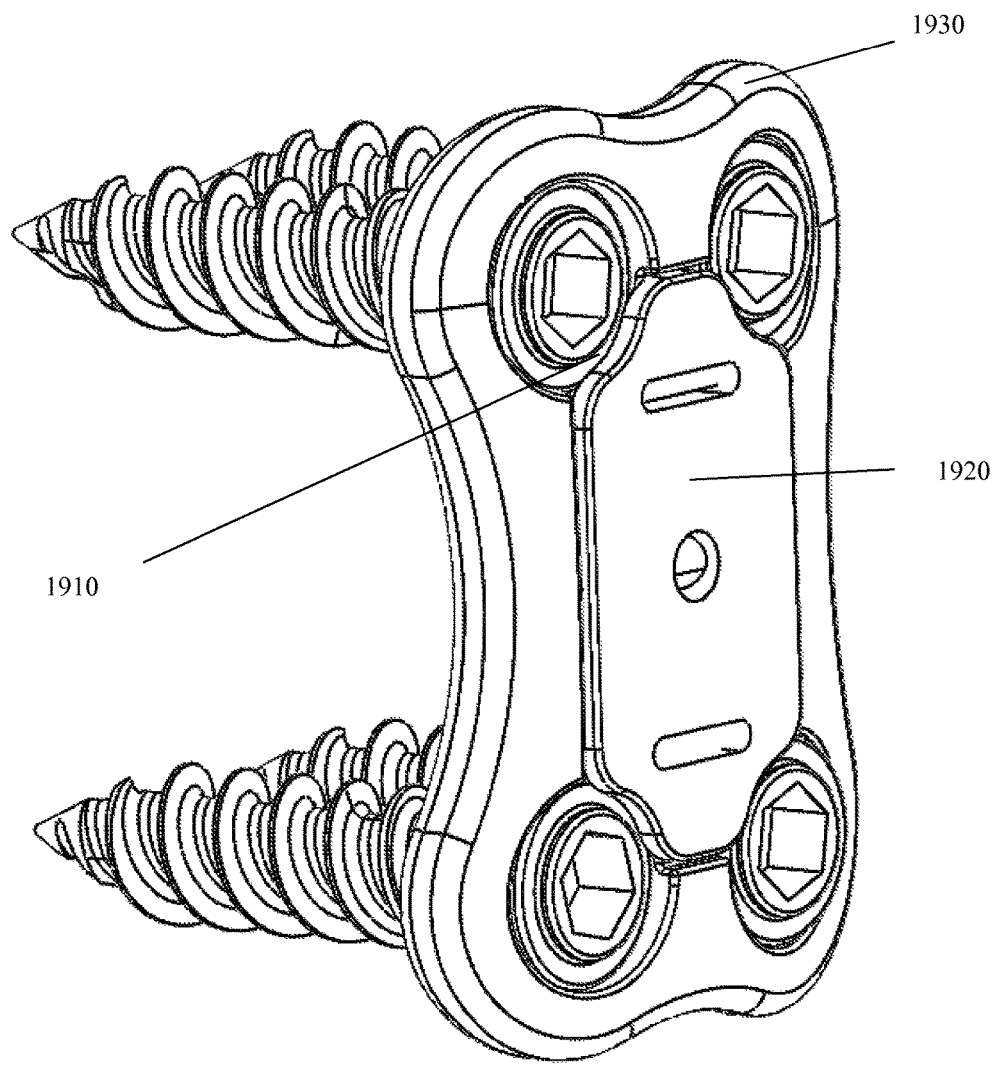
FIG. 19 shows an embodiment of a blocking cap coupled with an embodiment of a cervical plate through which are passing four screws.

FIG. 19 shows an embodiment of a blocking cap 1920 coupled with an embodiment of a cervical plate 1930 through which are passing four screws. FIG. 19 shows how this embodiment of a cervical cap 1920 coupled to this embodiment of a cervical plate 1930 would appear when positioned along the spine of a subject. The four screws shown would be penetrating vertebrae, with the top two screws penetrating a first vertebra and the bottom two screws penetrating a second vertebra. An interface 1910 is the point of contact of the blocking cap 1920 and a screw head, wherein the blocking cap 1920 is positioned within an indentation of the cervical plate 1930 so that the blocking cap 1920 sits flush against a portion of each of the screw heads and blocks the screws from backing out of the vertebra of the subject.

Figure 20:
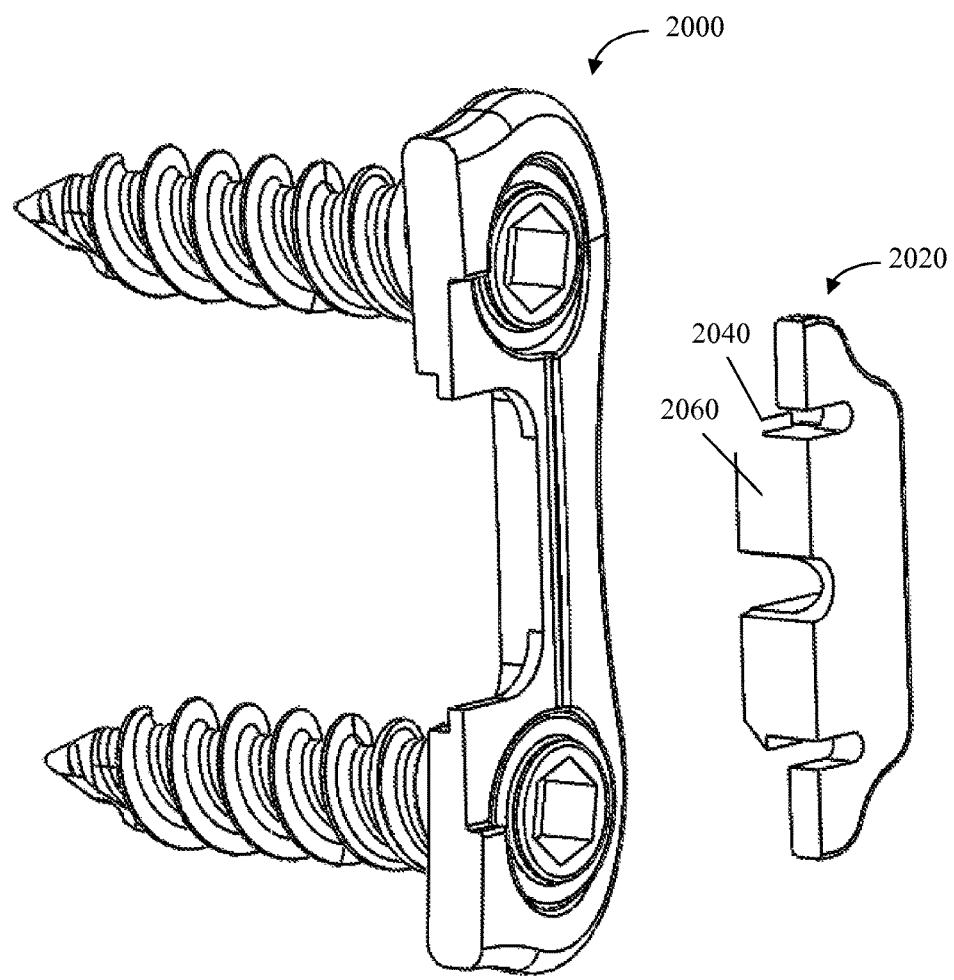
FIG. 20 shows a cross-sectional view of an embodiment of a cervical plate along with a cross section of an un-coupled blocking cap.

FIG. 20 shows a cross-sectional view of an embodiment of a cervical plate along with a cross section of an embodiment of an un-coupled blocking cap 2020. In some embodiments, a blocking cap 2020 comprises one or more blocking cap couplers 2060. In some embodiments, a blocking cap coupler 2060 further comprise a blocking cap engager 2040. In some embodiments, a blocking cap engager 2040 comprises a flange. In some embodiments, the flange is tapered.

Figure 21:
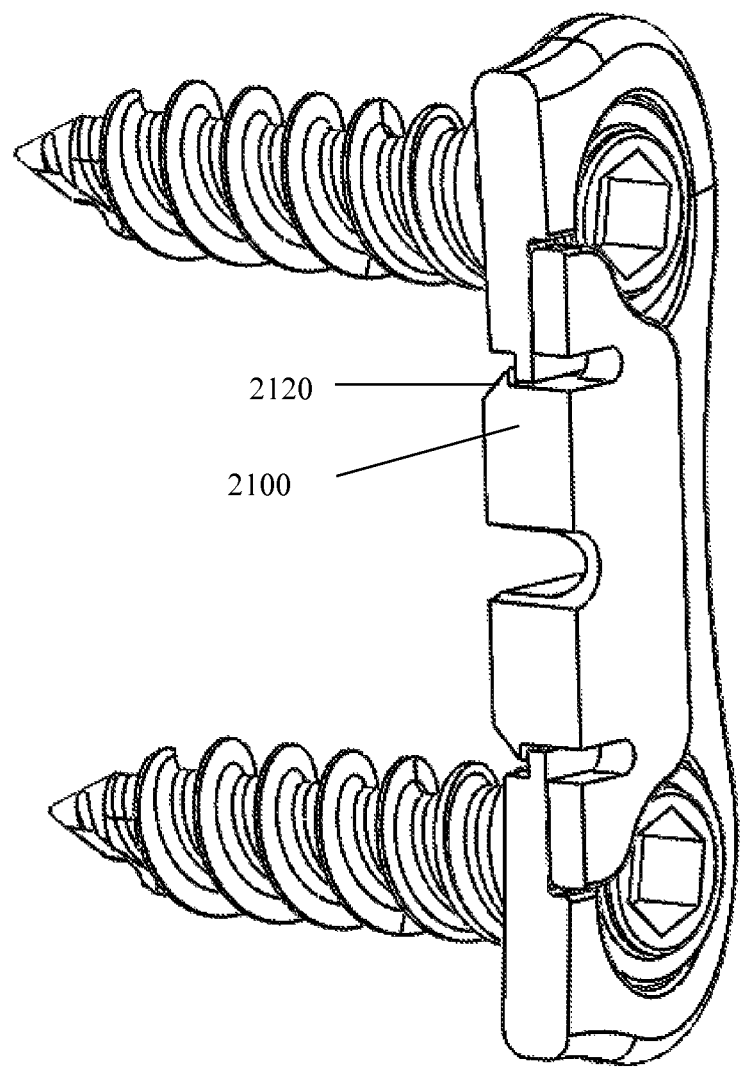
FIG. 21 shows a cross-sectional view of an embodiment of a cervical plate coupled with an embodiment of a blocking cap.

FIG. 21 shows a cross-sectional view of an embodiment of a cervical plate coupled with an embodiment of a blocking cap. In some embodiments, a blocking cap comprises one or more couplers 2100, and said one or more couplers 2100 may comprise one or more engagers 2120. In some embodiments, shown in FIG. 21, an engager 2100 comprises a tapered flange 2120. In some embodiments, the widest distance between two tapered flanges 2120 may be configured to be wider than an opening, as, for example, shown in FIG. 20, in a cervical plate so that when pushed together by, for example, a user the one or more flanges engage with one or more edges of the opening as shown. In some embodiments, the engagement of the one or more flanges 2120 of the blocking cap with the edge of the opening on the cervical plate resists the separation of the two coupled elements due to an outwardly directed force upon the blocking cap. In some embodiments, the respective widths of the opening of the cervical plate and between the widest point of the engagers 2120 on the blocking cap are configured so that the cervical plate and blocking cap may be snap-fitted together by a user pressing the two elements together.

Figure 22:
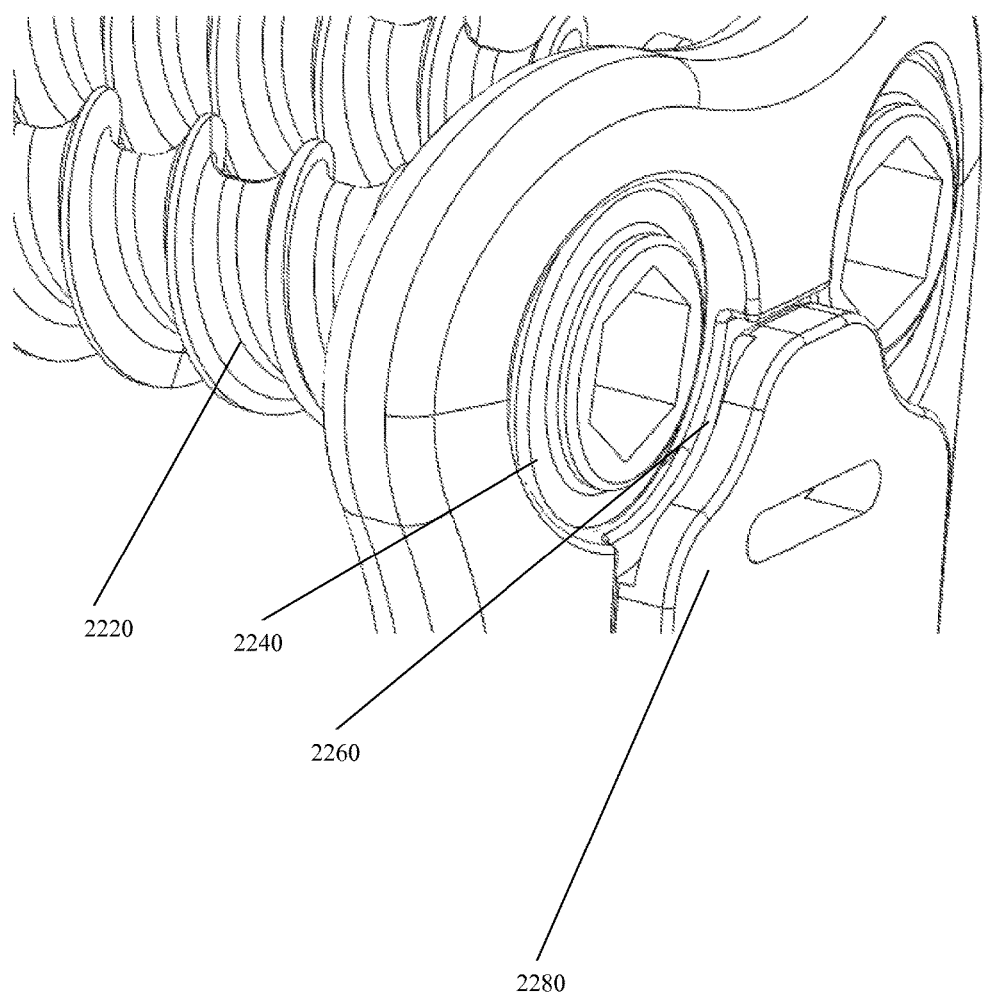
FIG. 22 shows a close up view of an embodiment of a cervical plate coupled with an embodiment of a blocking cap.

FIG. 22 shows a close up view of an embodiment of a cervical plate coupled with an embodiment of a blocking cap 2280. In some embodiments, a screw 2220 comprises a flat screw head 2240. In some embodiments, when the blocking cap 2280 couples with the cervical plate it creates an area of overlap 2260 of the blocking cap with the screw head 2240. In some embodiments, an overlap of at least a portion of a blocking cap 2280 with a screw head 2240 prevents a screw from backing out of a vertebra.

Figure 23:
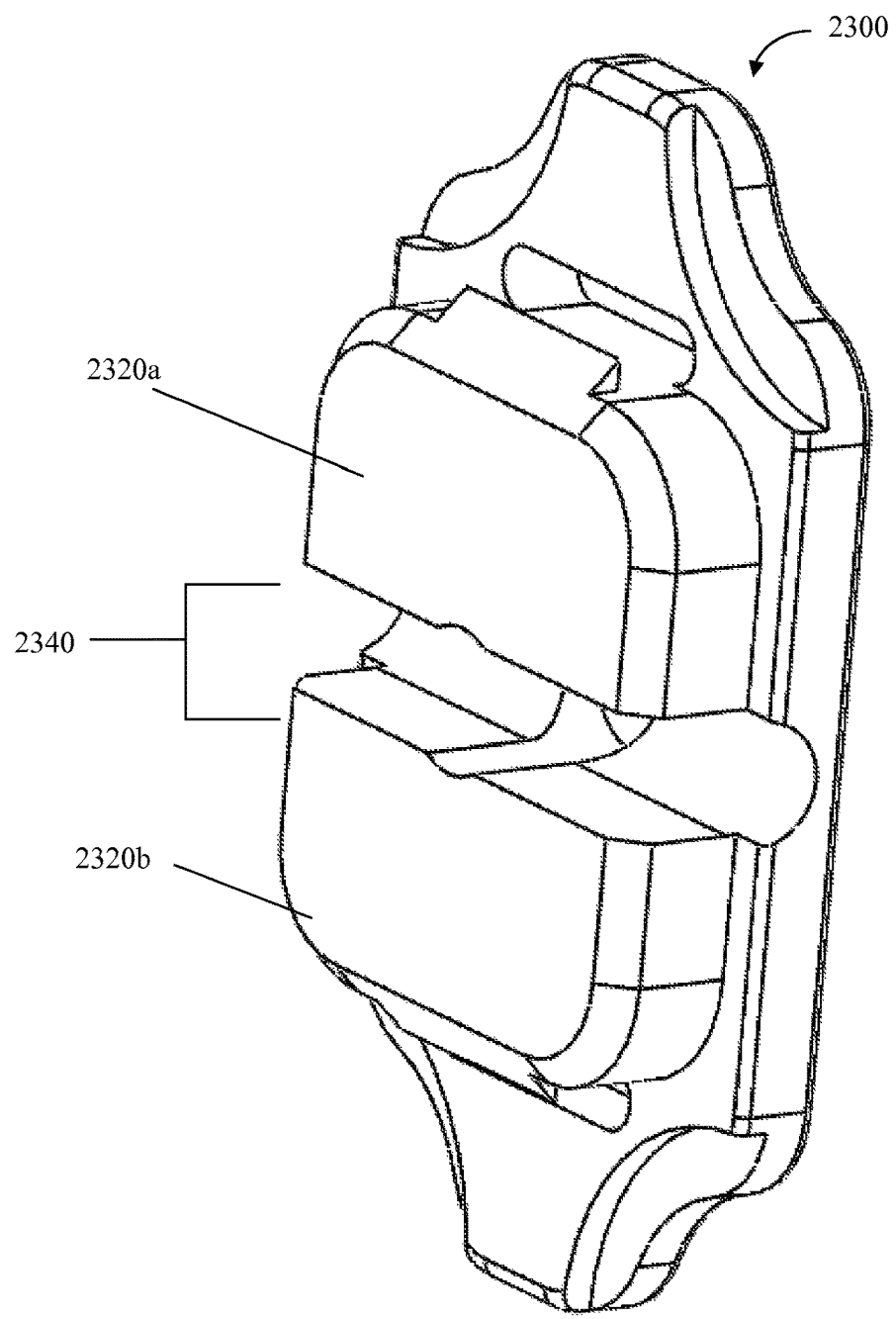
FIG. 23 shows a posterior view of an embodiment of the blocking cap.

FIG. 23 shows a posterior view of an embodiment of the blocking cap 2300. In some embodiments the blocking cap 2300 comprises one or more engagers 2320*a* and 2320*b*. In some embodiments, engagers 2320*a* and 2320*b* are separated by a gap 2340. In some embodiments, blocking cap 2300 comprises a relatively pliable material so that engagers 2320*a* and 2320*b* bend around the main axis of the gap 2340. Thus, in this embodiment, gap 2340 functions as a hinge around which the engagers 2320*a* and 2320*b* may bend either towards or away from each other to assist in snap-fitting the blocking cap 2300 to a cervical plate as described herein. For example, the engagers 2320*a* and 2320*b* may be bent by a user about gap 2340 so that the widest distance from one engager to the next is smaller than the widest diameter of an opening on a cervical plate configured to receive said blocking cap 2300, and then when the engagers 2320*a* and 2320*b* return to their normal unbent configuration the widest distance between the two engagers 2320*a* and 2320*b* may be wider than the widest diameter of the opening in the cervical plat thus snap-fitting the blocking cap 2300 with said cervical plate as described herein.

Figure 24:
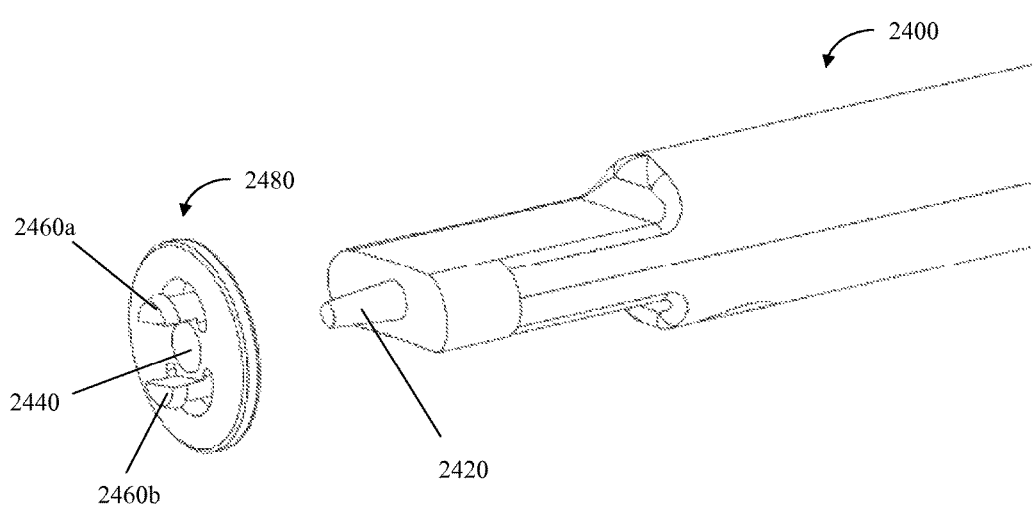
FIG. 24 shows a view of an embodiment of a delivery device along with an embodiment of a blocking cap.

FIG. 24 shows a view of an embodiment of a delivery device 2400 along with an embodiment of a blocking cap 2480. In some embodiments, the delivery device 2400 further comprises a blocking cap engager 2420. In some embodiments, the blocking cap engager on the delivery device comprises a tapered projecting portion 2420 that is configured to couple with a hole 2440 in a blocking cap 2480. In some embodiments, when a tapered projection portion 2420 is coupled with a hole 2440 in a blocking cap 2480 the insertion device 2400 may be used by a user to, for example, to deliver the blocking cap 2480 to a surgical site wherein, for example, a cervical plate (not shown in FIG. 24) is coupled to one or more cervical vertebra by cervical screws. In this embodiment, when the blocking cap 2480 is coupled to the cervical plate by, for example, a snap-fit connection, the blocking cap 2480 is more strongly coupled with the cervical plate than the engager 2420 on the delivery device 2400, and as a result, when the delivery device is withdrawn the engager 2420 on the delivery device disengages with the engager 2440 on the blocking cap 2480 thus decoupling the delivery device 2400 and the blocking cap 2480 (now coupled with the cervical plate). In some embodiments, the engager 2420 comprises a threaded element that threadably attaches to a threaded engager on the blocking cap 2480. In some embodiments the engager on the delivery device 2400 is configured to snap-fit with the blocking cap 2480. In some embodiments, blocking cap 2480 comprises a coupling mechanism configured to couple the blocking cap 2480 with a cervical plate, said coupling mechanism comprising of one or more engagers 2460*a* and 2460*b*. In some embodiments, said coupling mechanism is configured to couple the blocking cap 248 to a cervical plate in a snap-fit fashion as described herein.

Figure 25:
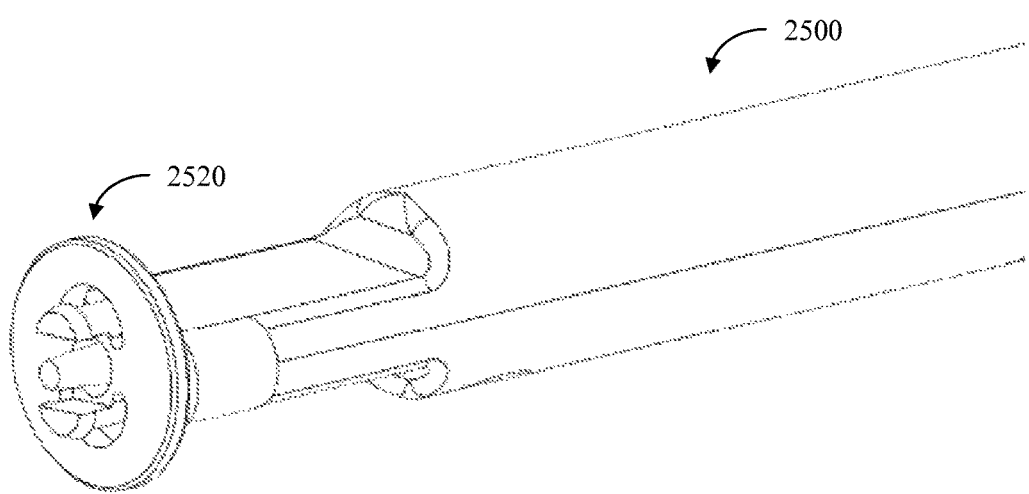
FIG. 25 shows a delivery device coupled with a blocking cap.

FIG. 25 shows a delivery device 2500 coupled with a blocking cap 2520.

Figure 26:
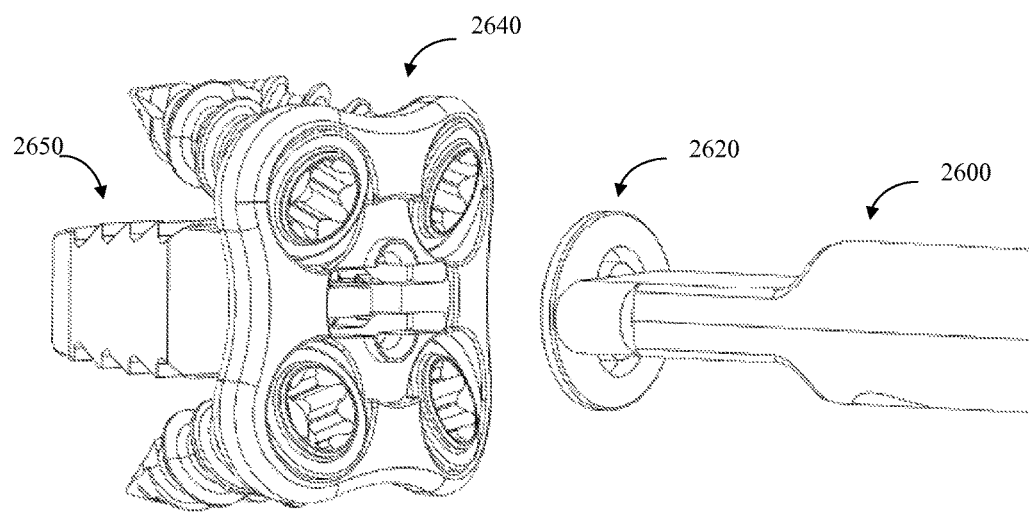
FIG. 26 shows a delivery device 2600 coupled with blocking cap that is being delivered to a cervical plate that is coupled to an in position cervical implant.

FIG. 26 shows a delivery device 2600 coupled with blocking cap 2620 that is being delivered to a cervical plate 2640 that is coupled to an in position cervical implant 2660. The vertebra are not shown in FIG. 26, but, for example, in situ, a cervical implant 2660 may be positioned between two cervical vertebra, for example, C5 and C6, and a cervical plate 2640 may be coupled to the in position cervical implant 2640 as described herein. Further in this example, said cervical plate 2640 may be coupled or fixed to C5 and C6 by one or more surgical screws. Further still in this example, a blocking cap 2620 may be delivered by a delivery device 2600—to which the blocking cap 2620 is coupled or engaged—to the surgical site where the cervical plate 2640 is coupled with the implant 2660 as described. In some embodiments, the blocking cap 2620 may be snap-fit coupled with the cervical plate 2640 as described herein by, for example, a user pushing the blocking cap 2620 and cervical plate 2640 together using the delivery device 2600 so that their respective couplers engage.

Figure 27:
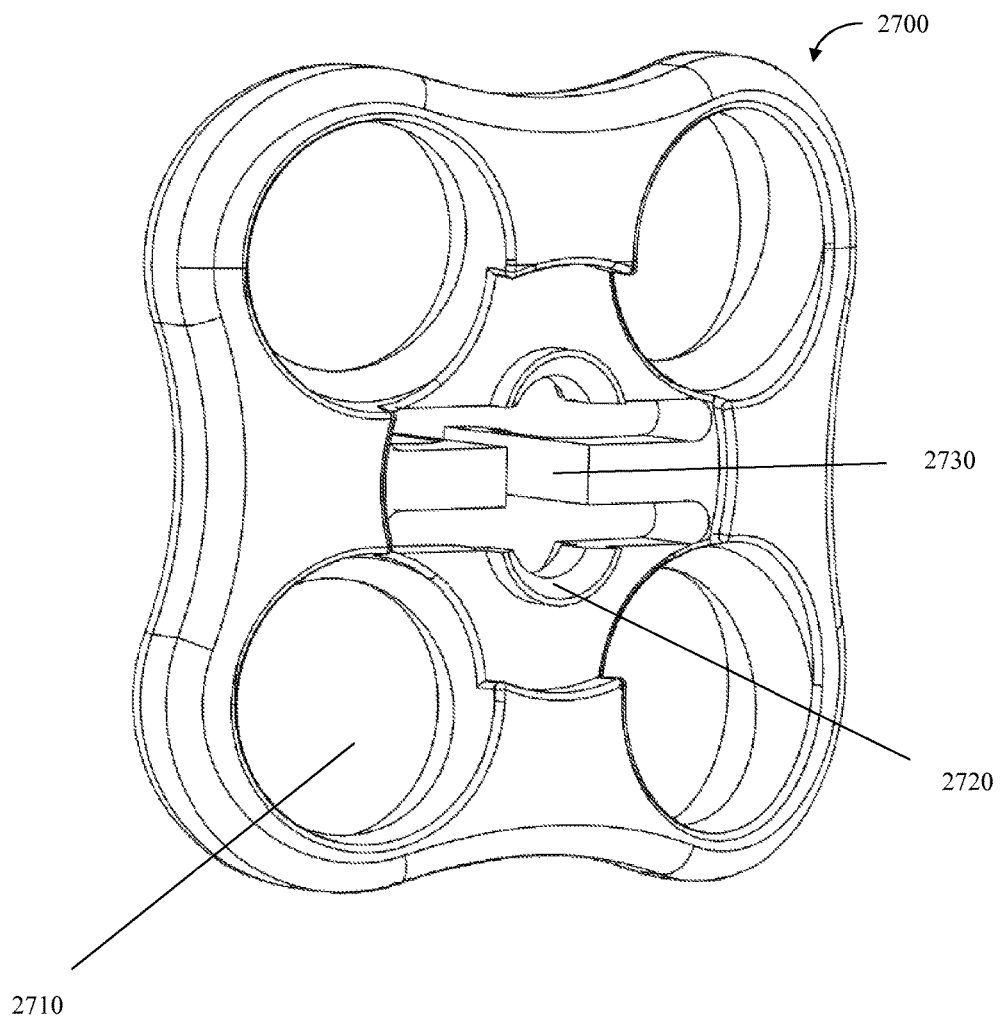
FIG. 27 shows an anterior view of an embodiment of a cervical plate.

FIG. 27 shows an anterior view of an embodiment of a cervical plate 2700. Shown is a prong 2730 that forms a coupling mechanism for coupling with an implant (not shown). Surface 2720 is shaped to conform to the shape of an embodiment of a blocking cap (not shown). Screw hole 2710 is configured to receive and seat a screw.

Figure 28:
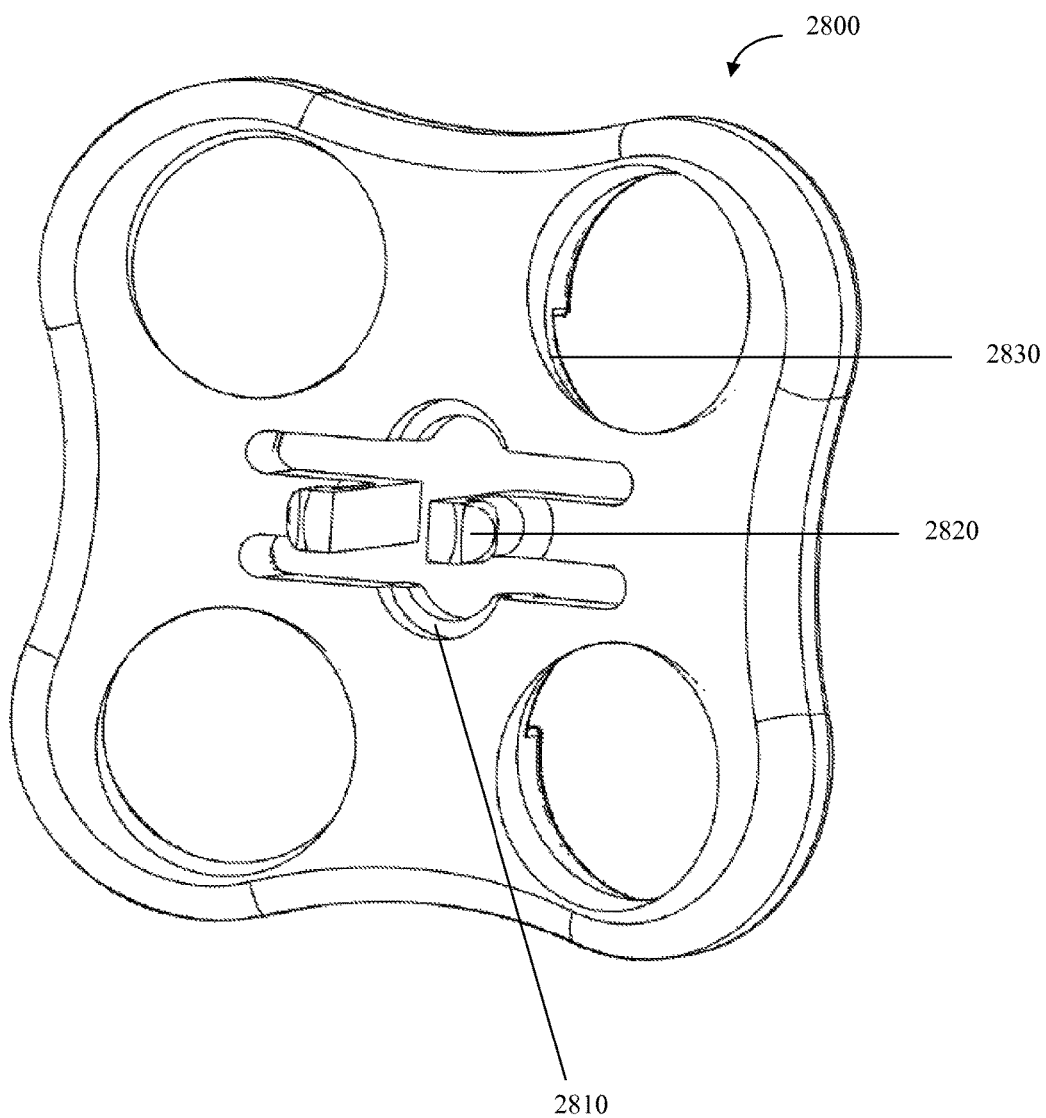
FIG. 28 shows a posterior view of an embodiment of a cervical plate.

FIG. 28 shows a posterior view of an embodiment of a cervical plate 2800. Prong head 2820 is part of a coupling mechanism for coupling the cervical plate 2820 to an implant (not shown). Surface 2810 is shaped to receive a blocking cap (not shown). Indentation 2830 is configured to receive a blocking cap (not shown) so that it is essentially flush against a portion of a screw head within the screw hole of the cervical plate 2800.

Figure 29:
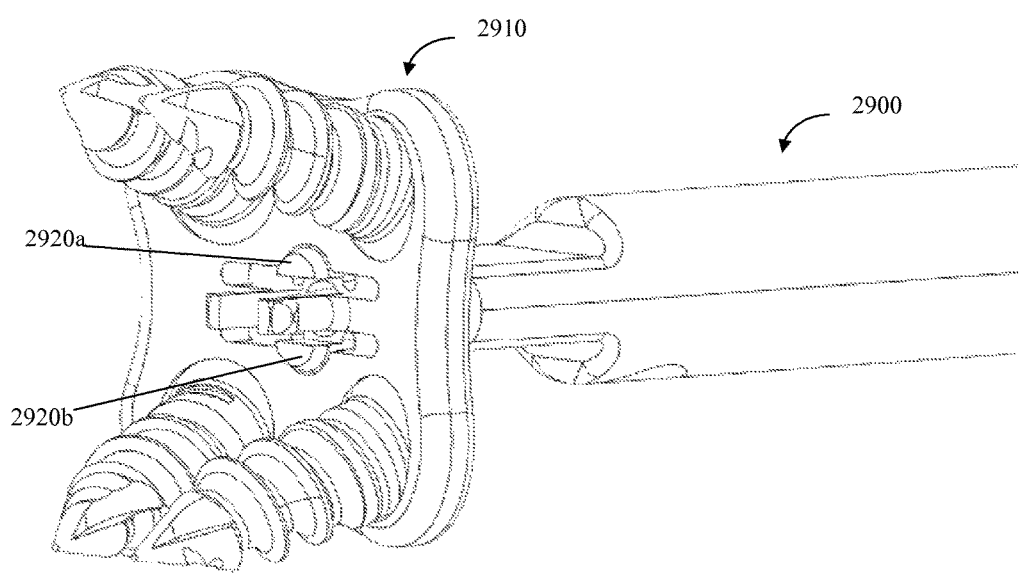
FIG. 29 shows a posterior view of an embodiment of a cervical plate coupled with a blocking cap that is coupled with a delivery device.

FIG. 29 shows a posterior view of an embodiment of a cervical plate 2910 coupled with a blocking cap that is coupled with a delivery device 2900. In some embodiments, a delivery device 2900 coupled with a blocking cap delivers the blocking cap to the cervical plate as described herein. In some embodiments, engagers 2920*a* and 2920*b* of the blocking cap couple with openings on the cervical plate in a snap-fit fashion as described herein.

Figure 30:
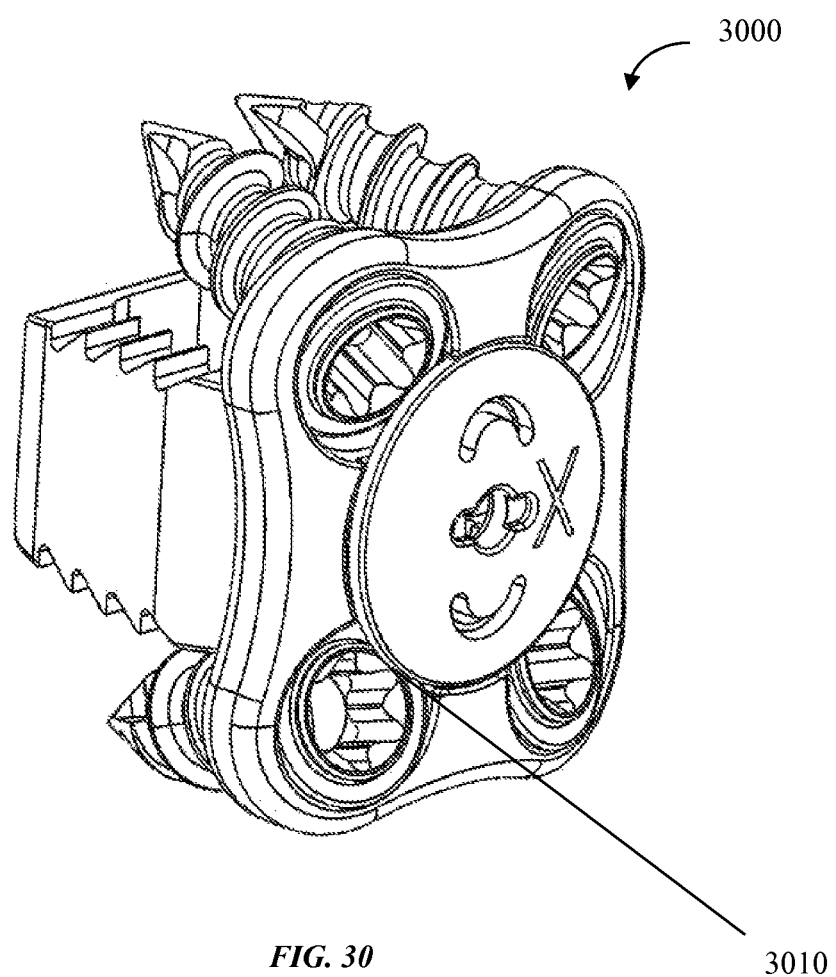
FIG. 30 shows an anterior view of an embodiment of a cervical plate coupled with an implant, and further coupled with a blocking cap as described herein.

FIG. 30 shows an anterior view of an embodiment of a cervical plate 3000 coupled with an implant, and further coupled with a blocking cap as described herein. Interface 3010 shows an interface of a blocking cap positioned essentially flush against a portion of a screw head so as to prevent the screw head from backing out.

Figure 31:
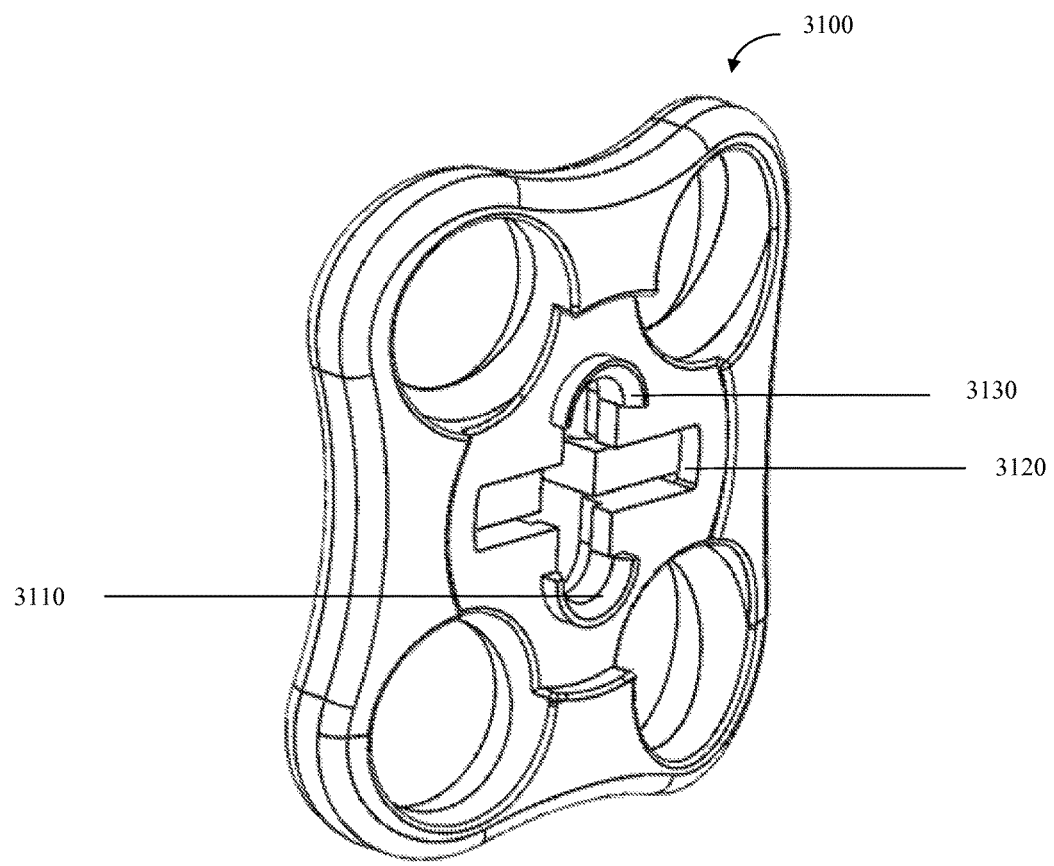
FIG. 31 shows an anterior view of an embodiment of a cervical plate.

FIG. 31 shows an anterior view of an embodiment of a cervical plate 3100. Surfaces 3130 and 3110 are configured to receive engagers of a blocking cap. Opening 3120 is configured to receive a protrusion of a blocking cap.

Figure 32:
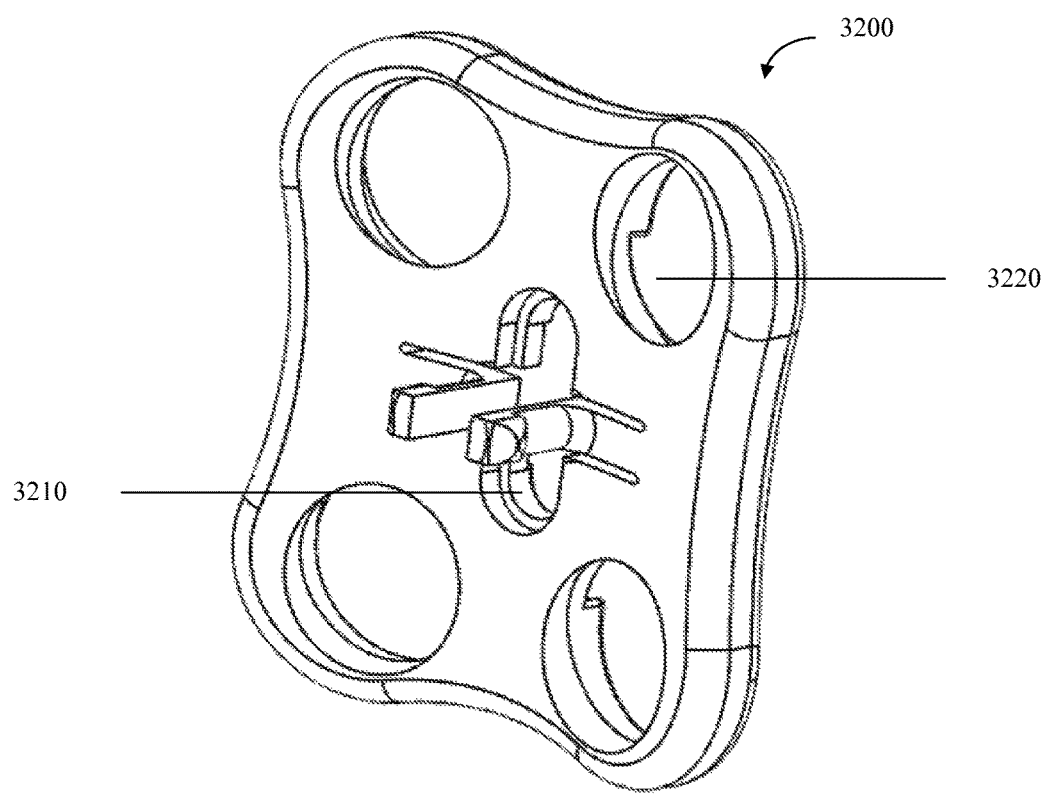
FIG. 32 shows an anterior view of an embodiment of a cervical plate.

FIG. 32 shows a posterior view of an embodiment of a cervical plate 3200. Screw hole 3220 is configured to receive a screw. Surface 3210 is shaped to receive and seat a blocking cap engager.

Figure 33:
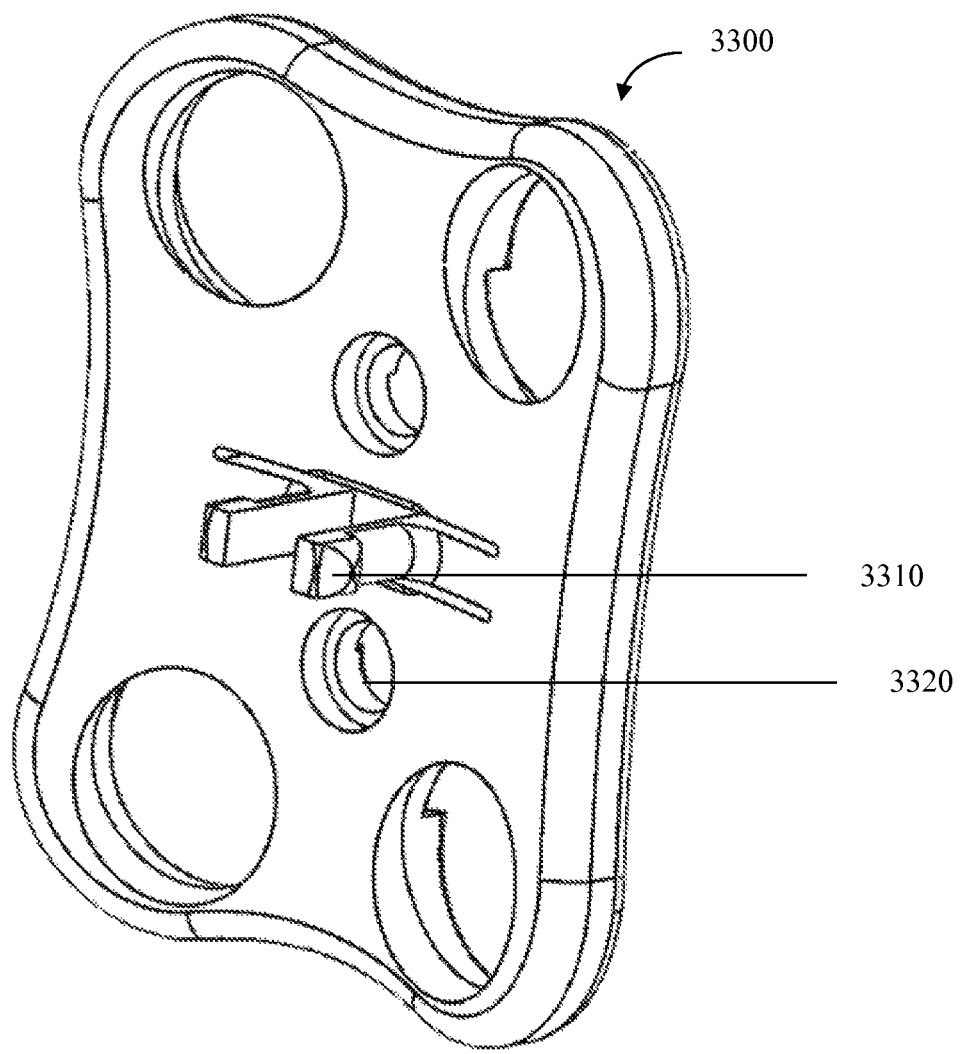
FIG. 33 shows a posterior view of an embodiment of a cervical plate.

FIG. 33 shows a posterior view of an embodiment of a cervical plate 3300. Prong head 3310 forms a coupling mechanism for coupling the cervical plate 3300 to an implant as described herein. Hole 3320 is shaped to receive and seat a blocking cap engager of an embodiment of a blocking cap (not shown).

Figure 34:
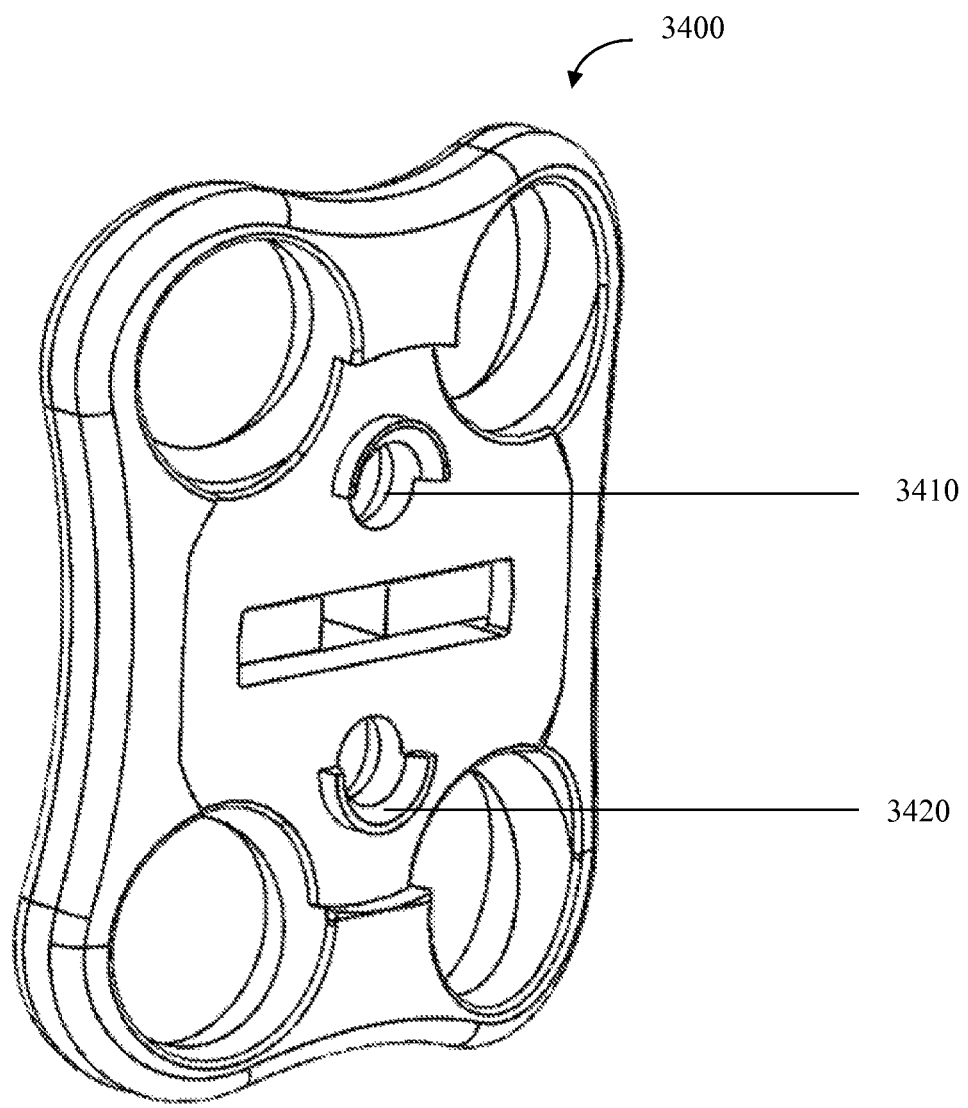
FIG. 34 shows an anterior view of an embodiment of a cervical plate.

FIG. 34 shows an anterior view of an embodiment of a cervical plate 3400. Surface 3420 and opening 3410 are configured to receive engagers of a blocking cap (not shown).

What is claimed is:

1. A system for use in surgical treatment of cervical disc disease comprising:
   a) a cervical implant comprising a cervical implant coupler, wherein said cervical implant is configured to be positioned between a first and a second cervical vertebra;
   b) a cervical plate having an anterior surface that faces away from the cervical implant when coupled to the cervical implant and a posterior surface that faces towards the cervical implant when coupled to the cervical implant, the cervical plate configured to couple with the cervical implant coupler in a snap-fit fashion, the cervical plate comprising:
      i. one or more surgical screw holes, wherein each of the one or more surgical screw holes are configured to receive a screw; and
      ii. a first recess having a first edge and a second edge, the second edge positioned opposite the first edge; and
      iii. a second recess having a third edge and a fourth edge, the fourth edge positioned opposite the third edge;
   c) a blocking cap configured to couple with the first recess and the second recess in a snap-fit fashion, the blocking cap comprising:
      i. a first prong comprising a first prong head configured to snap-fit with the first recess; and
      ii. a second prong comprising a second prong head configured to snap-fit with the second recess;
   wherein when the first prong snap-fits with the first recess and the second prong snap-fits with the second recess, (a) the first and the second edges are each positioned on opposite sides of and adjacent to the first prong, (b) the third and the fourth edges are each positioned on opposite sides of and adjacent to the second prong, and (c) the first and the second prong heads each engage with the posterior surface of the cervical plate so that the blocking cap is secured in place relative to the cervical plate.

2. The system of claim 1, wherein the one or more screw holes comprise one or more angled interior edges that are configured to seat a received screw at an angle that is not perpendicular to the cervical plate when the cervical plate is coupled with the cervical implant.

3. The system of claim 1, wherein the cervical plate comprises two prongs, wherein the widest distance between the two prongs comprises a first width when the prongs are not compressed, and wherein the widest distance between the two prongs comprises a second width when the two prongs are compressed, wherein the second width is smaller than the first width, and wherein the second width is smaller than at least one width of an opening in the cervical implant coupler.

4. The system of claim 1, wherein the blocking cap is configured to prevent the backing out of one or more screws when coupled with a cervical plate.

5. The system of claim 1, wherein the cervical plate further comprises a recessed surface configured to receive the blocking cap and seat the blocking cap at least partially directly over one or more screws seated within the one or more holes in the cervical plate.

6. The system of claim 1, wherein the cervical plate comprises one or more materials selected from the group consisting of polyether ether ketone (PEEK), carbon fiber-reinforced polymer, carbon fiber-reinforced plastic, carbon fiber-reinforced thermoplastic, glass fiber-reinforced polymer, glass fiber-reinforced plastic and polyaryletherketone.

* * * * *